US008552254B2

(12) United States Patent
Wiles et al.

(10) Patent No.: US 8,552,254 B2
(45) Date of Patent: *Oct. 8, 2013

(54) METHODS FOR MAINTAINING GENETIC STABILITY OF INBRED ANIMAL STRAINS

(75) Inventors: Michael V. Wiles, Mount Desert, ME (US); Robert Taft, Southwest Harbor, ME (US); Eva M. Eicher, Seal Cove, ME (US); Shannon Byers, Lamoine, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 429 days.

This patent is subject to a terminal disclaimer.

(21) Appl. No.: 12/606,047

(22) Filed: Oct. 26, 2009

(65) Prior Publication Data

US 2010/0113867 A1     May 6, 2010

Related U.S. Application Data

(63) Continuation-in-part of application No. 12/536,909, filed on Aug. 6, 2009, which is a continuation of application No. 10/915,840, filed on Aug. 11, 2004, now Pat. No. 7,592,501.

(60) Provisional application No. 60/497,451, filed on Aug. 22, 2003.

(51) Int. Cl.
*C12N 15/00* (2006.01)
*A01K 67/00* (2006.01)
*A01K 67/027* (2006.01)

(52) U.S. Cl.
USPC ................................... 800/21; 800/8; 800/18

(58) Field of Classification Search
USPC ................................................ 800/8, 18, 21
See application file for complete search history.

(56) References Cited

U.S. PATENT DOCUMENTS

| 5,160,312 A | 11/1992 | Voelkel |
| 5,758,763 A | 6/1998 | Sanda |
| 2002/0131957 A1 | 9/2002 | Gavin |
| 2008/0026361 A1 | 1/2008 | Ostermeier et al. |

FOREIGN PATENT DOCUMENTS

| EP | 0710439 A2 | 5/1996 |
| WO | WO 91/12719 A1 | 9/1991 |
| WO | WO 97/37009 | 10/1997 |
| WO | WO 00/04186 | 1/2000 |
| WO | WO 00/11147 | 3/2000 |
| WO | WO 01/84920 A1 | 11/2001 |
| WO | WO 01/87062 A2 | 11/2001 |

OTHER PUBLICATIONS

Houdebine, 1997, Transgenic Animals, OPA Publishers, Book Excerpt, 4 pages total.*

Bailey, Donald, W., "Sources of Subline Divergence and their Relative Importance for Sublines of Six Major Inbred Strains of Mice", *Origins of Inbred Mice*. The Jackson Laboratory, Aug. 13, 2007 http://www.informatics.jax.org/morsebook/frames/frame15.shtml.
Bailey DW, "How pure are inbred strains of mice?", 1982, vol. 8, pp. 210-214.
Bailey DW, "Genetic Drift: the problem and its possible solution by frozen-embryo storage", 1977, Ciba Found Symp., pp. 291-303.
Butler, L. et al., "Genetic analysis of the BB/W diabetic rat", Can J. Genet. Cytol. 25:7-15 (1983).
Byers, Shannon L. et al., Performance of ten inbred mouse strains following assisted reproductive technologies (ARTs), Theriogenology 65 (2006) 1716-1726.
Candy, C.J., et al., "Restoration of a normal reproductive lifespan after grafting of cryopreserved mouse ovaries", Human Reproduction, 15(6):1300-1304 (2000).
Chiu, T.T.Y., et al., "Effects of myo-inositol on the in-vitro maturation and subsequent development of mouse oocytes," Human Reproduction, 18(2):408-416(2003).
Cseh, S., "Vitrification of mouse embryos in two cryoprotectant solutions", 1999, Theriogenology, vol. 52, pp. 103-113.
Eggan, K., et al., "Male and female mice derived from the same embryonic stem cell clone by tetraploid embryo complementation", Nature Biotechnology, 20:455-459 (2002).
Hirabayahsi et al., 1997, Exp. Anim., vol. 46, No. 2, pp. 111-115.
Huang, Kuo-Yu et al., "Functionality of cryopreserved juvenile ovaries from mutant mice in different genetic background strains after allotransplantation", Cryobiology (2009), doi:10.1016/j.cryobio1.2009.10.003.
Hubner, K., et al., "Derivation of Oocytes from Mouse Embryonic Stem Cells", Science, 300:1251-1256 (2003).
Johnson, K.R., et al., "A Major Gene Affecting Age-Related Hearing Loss is Common to at Least Ten Inbred Strains of Mice", Genomics, 70:171-180 (2000).
Kimura, Y., et al., "Mouse oocytes injected with testicular spermatozoa or round spermatids can develop into normal offspring," Development, 121:2397-2405 (1995).
Kubota, H., et al., "Spermatogonial stem cells share some, but not all, phenotypic and functional characteristics with other stem cells", PNAS, 100(11):6487-6492 (2003).
Liu, J., "Fertilization of mouse oocytes from in vitro-matured preantral follicles using classical in vitro fertilization or intracytoplasmic sperm injection", 2002, Biology of Reproduction, vol. 67, pp. 575-579.
Mobraaten, LE., 1986, J. In Vitro Fert. Embryo Transfer, vol. 3, No. 1, pp. 28-32.
Nagy, A., et al., "Derivation of completely cell culture-derived mice from early-passage embryonic stem cells", Proc. Natl. Acad. Sci., 90:8424-8428 (1993).
Nakagata K., "Cryopreservation of mouse spermatozoa", Mammalian Genome, vol. 11, pp. 572-576, 2000.
Nomura et al., "Establishment and Preservation of Reference Inbred Strains of Rats for General Purpose Use: Report on U.S. —Japan non-Energy Research and Development Cooperation: Laboratory Animal Science", ILAR Journal Online 33(3):1-3 (1991).
O'Brien, M.J., et al., "A Revised Protocol for In Vitro Development of Mouse Oocytes from Primordial Follicles Dramatically Improves Their Developmental Competence", Biology of Reproduction, 68:1682-1686 (2003).

(Continued)

*Primary Examiner* — Peter Paras, Jr.
*Assistant Examiner* — David A Montanari
(74) *Attorney, Agent, or Firm* — Wolf, Greenfield & Sacks, P.C.

(57) ABSTRACT

The present invention provides novel methods of maintaining genetic stability of non-human animal inbred strains. In the methods, pedigree-tracked cryopreserved embryos or gametes or pre-gametes derived from a foundation colony are produced and used to re-establish the foundation colony at appropriate intervals.

29 Claims, 7 Drawing Sheets

(56) References Cited

OTHER PUBLICATIONS

Ostermeier, G. Charles et al., "Conserving, Distributing and Managing Genetically Modified Mouse Lines by Sperm Cryopreservation", PLoS One, Jul. 2008, vol. 3, Issue 7, pp. 1-8.

Sato, M., et al., "Comparison of Intrabursal Transfer of Spermatozoa, A New Method for Artificial Insemination in Mice, With Intraoviductal Transfer of Spermatozoa", Journal of Assisted Reproduction and Genetics, 19(11):523-530(2002).

Specht, C.G., et al., "Deletion of the alpha-synuclein locus in a subpopulation of C57BL/6J inbred mice", BMC Neuroscience, 2:11 (2001).

Sztein, J., et al., "Cryopreservation and Orthotopic Transplantation of Mouse Ovaries: New Approach in Gamete Banking", Biology of Reproduction, 58:1071-1074 (1998).

Sztein, J.M., et al., "Comparison of Permeating and Nonpermeating Cryoprotectants for Mouse Sperm Cryopreservation", Cryobiology, 41:28-39 (2001).

Taft, Robert A. et al., "Know thy Mouse", TRENDS in Genetics (2006), doi:10.1016/j.tig.2006.09.010.

Toyooka, Y., et al., "Embryonic stem cells can form germ cells in vitro", 100(20):11457-11462 (2003).

Ueda, O., "Factors affecting the efficiency of chimera production by coculture of zona-free embryos with frozen-thawed embryonic stem cells in mice", 1995, J. Reprod. Dev., vol. 41, pp. 181-186.

Wotjak, C.T., "C57Black/BOX? The importance of exact mouse strain nomenclature",Trends in Genetics, 19(4):183-184 (2003).

International Search Report for PCT/US2004/026003 dated Sep. 25, 2008.

Denning, C., et al., "New frontiers in gene targeting and cloning: success, application and challenges in domestic animals and human embryonic stem cells", Reproduction, vol. 126, pp. 1-11 (2003).

Moreadith, R. W. et al., ,, Gene targeting in embryonic stem cells: the new physiology and metabolism, J. Mol. Med., vol. 75 pp. 208-216 (1997).

Prelle, K. et al., "Establishment of Pluripotent Cell Lines from Vertebrate Species—Present Status and Future Prospects", Cell Tissues Organs, vol. 165, pp. 220-236 (1999).

Smith, K., "Gene transfer in higher animals: theoretical considerations and key concepts", Journal of Biotechnology, vol. 99, pp. 1-22 (2002).

Ehling, C. et al., *Genetic Structure and Diversity of the gene reserve of the old type German Black Pied cattle*, vol. 71(2), pp. 130-146 (1999).

Hioki, K. et al., *Strain Maintenance by Cryopreservation of Fertilized Eggs (2-Cell Embryos) of Inbred Strain Rats*, H4-6, pp. 4-7 (1995).

Ino, T., *Study of Experimental Animals*, Youken-Do, pp. 26-30 (1982).

Pisenti, T.M., et al., *Avian Genetic Resources at Risk: An Assessment and Proposal for Conservation of Genetic Stocks in the USA and Canada*, Genetic Resources Conservation Program, Report No. 20, Sep. 1999.

Report of Grant-in-Aid for Scientific Research on Cancer Priority Areas by The Ministry of Education, Science, Sports and Culture; 1997, Scientific Research on Priority Areas related to Cancer Research, pp. 29-30 (1998).

Goto, K. et al., *Effects of Cryopreservation of Mouse Embryos and In Vitro Fertilization on Genotypic Frequencies in Colonies*; Molecular Reproduction and Development 62: 307-311 (2002).

\* cited by examiner

Figure 1. Generating embryos derived from a foundation colony to be used for maintaining genetic stability of an inbred strain.
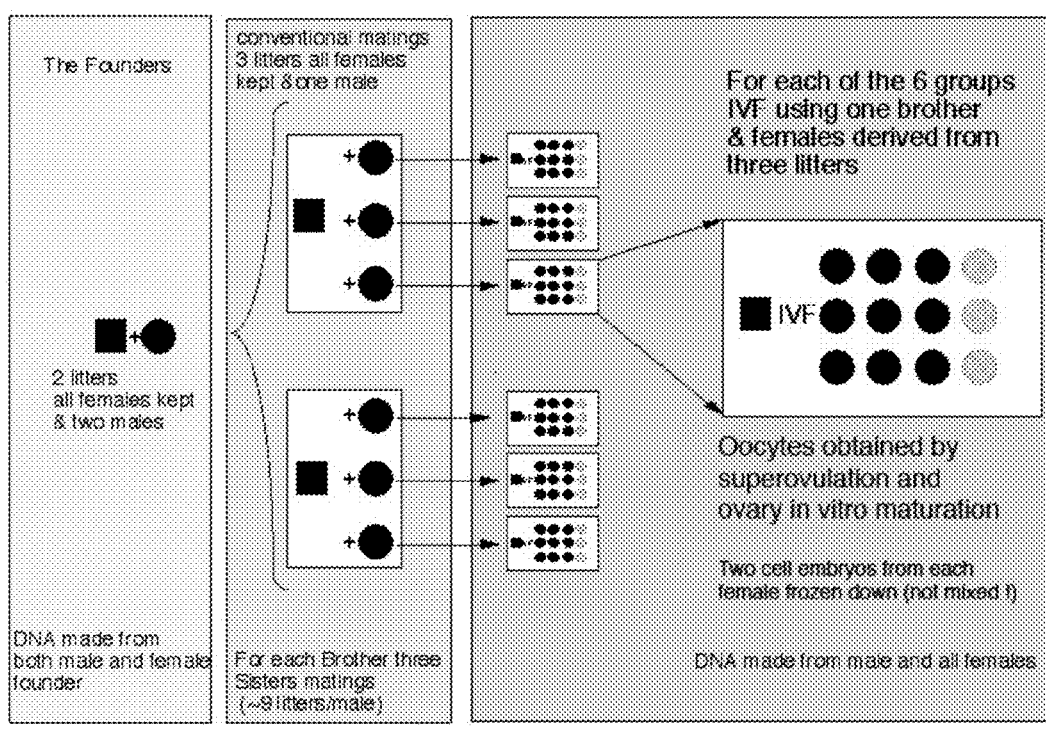

Figure 2: Serial Transfer of fresh BALB/cByJ Ovaries (OT = ovary transplant)
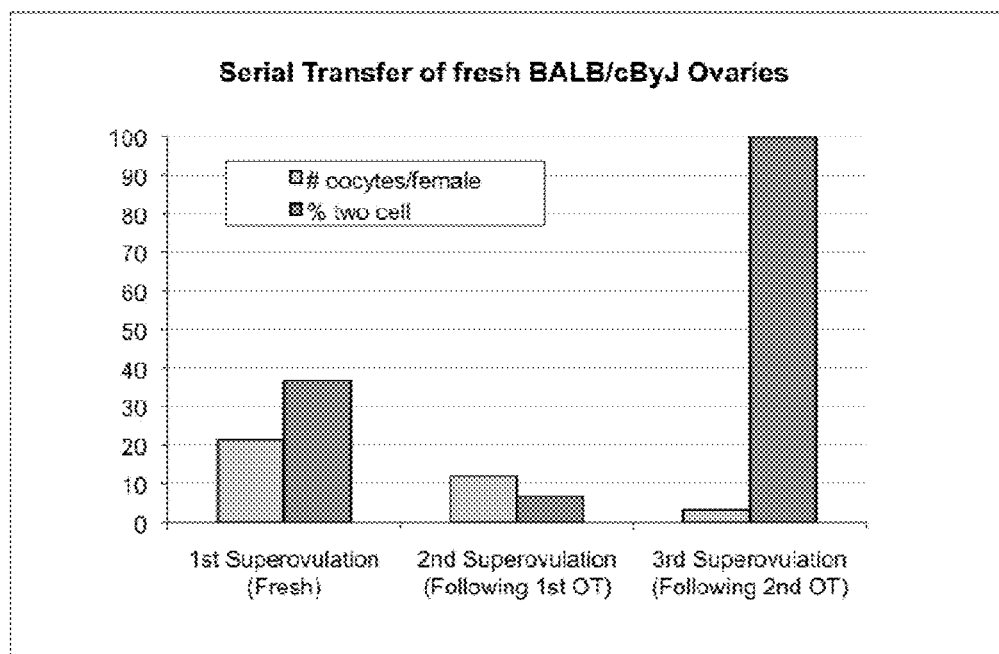

Figure 3: Serial Transfer of Frozen BALB/cByJ Ovaries (OT = ovary transplant)
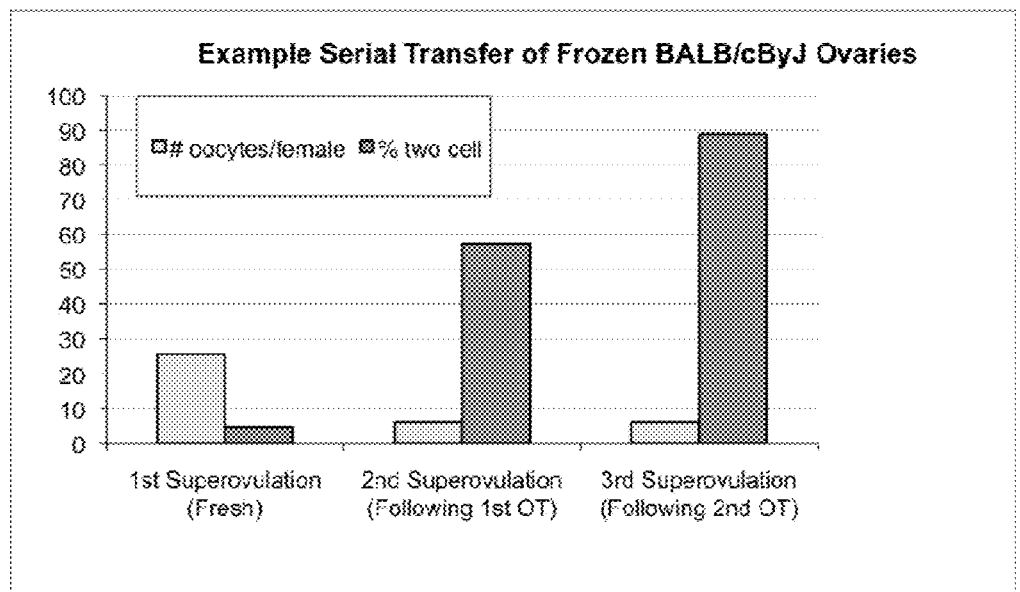

Figure 4: Numbers of Oocytes isolated after serial ovary transplantation of fresh C57BL/6J ovaries
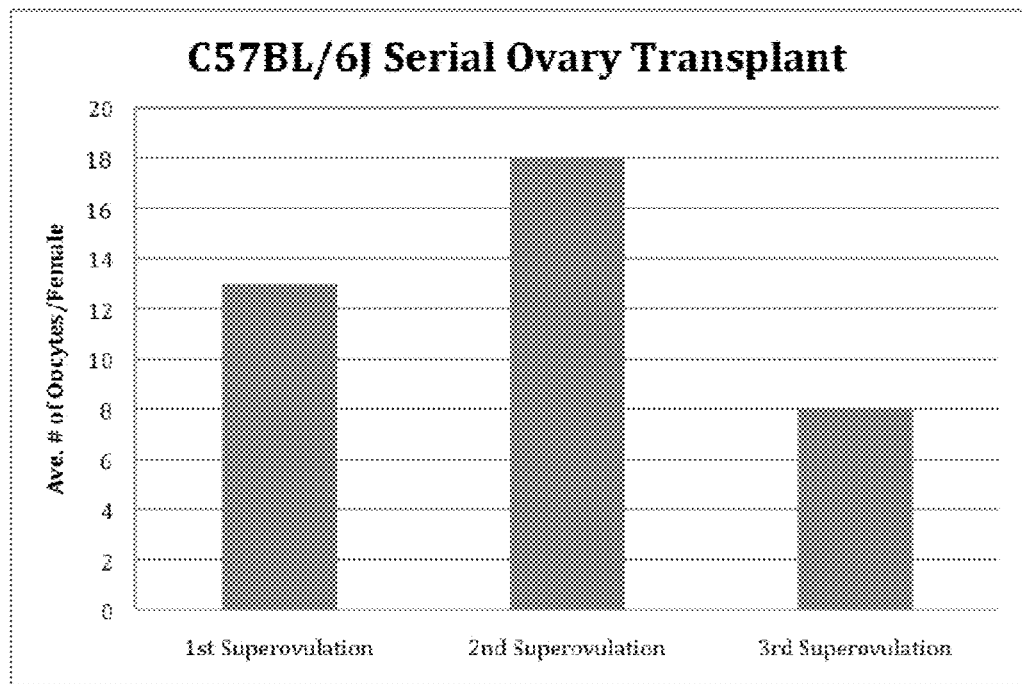

Figure 5: Fertilization Rates after Serial Ovary transplantation of fresh C57BL/6J ovaries
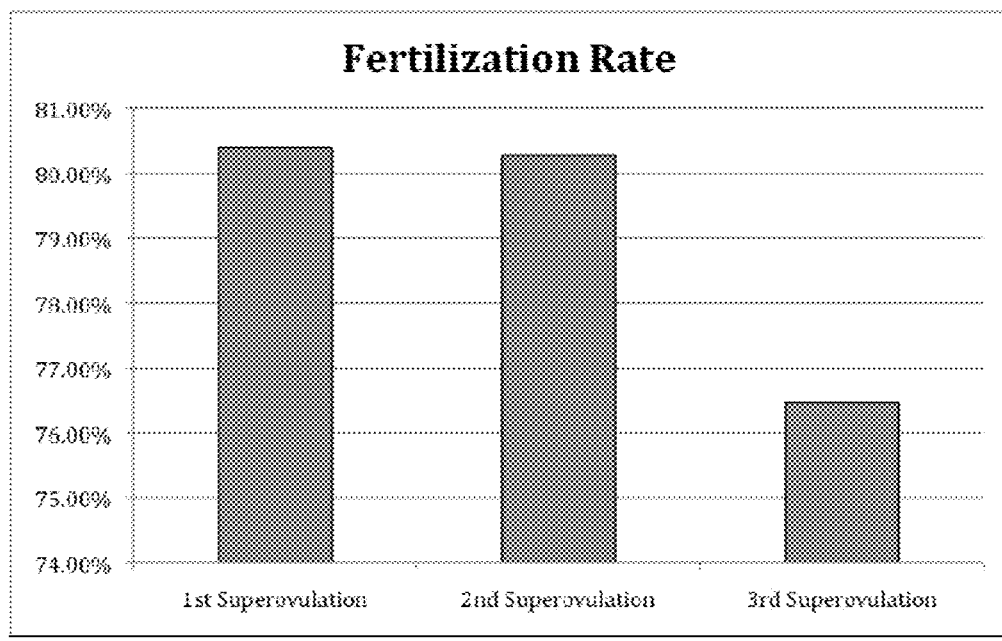

Figure 6: Mouse ovary dissected into 16 fragments and compared to whole ovary
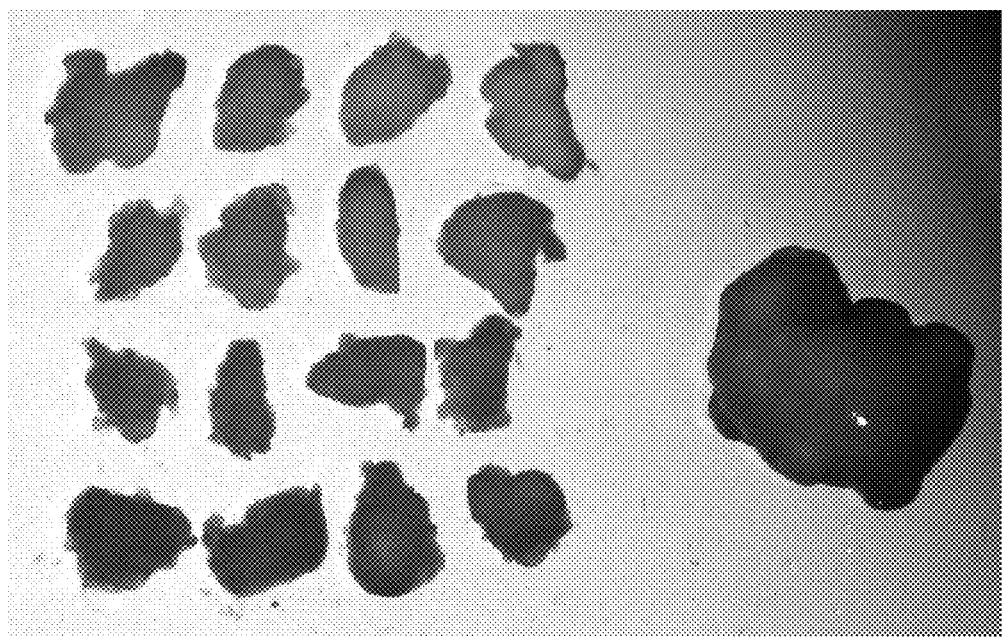

Figure 7: Mouse ovary dissected into 32 fragments and compared to whole ovary
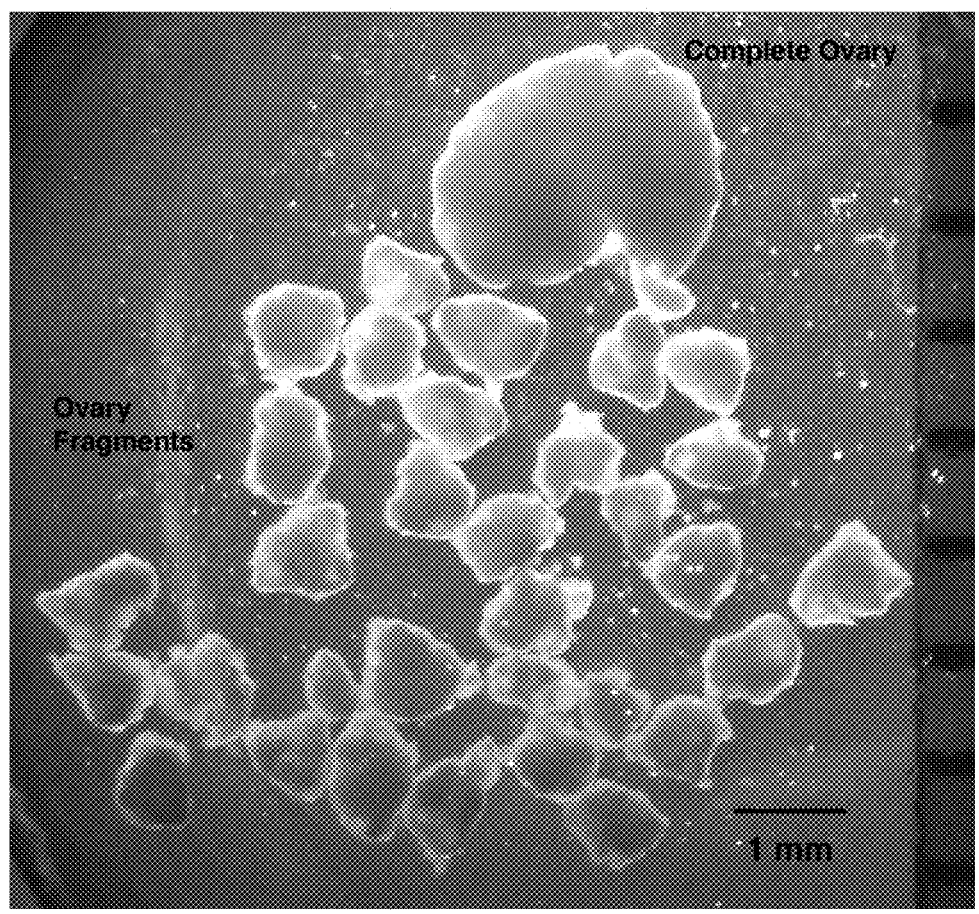

METHODS FOR MAINTAINING GENETIC STABILITY OF INBRED ANIMAL STRAINS

CROSS-REFERENCE TO RELATED APPLICATIONS

This application is a continuation-in-part of U.S. application Ser. No. 12/536,909, filed Aug. 6, 2009, which is a continuation application of U.S. application Ser. No. 10/915,840, filed on Aug. 11, 2004, now U.S. Pat. No. 7,592,501, which claims the benefit of U.S. Provisional Application No. 60/497,451, filed Aug. 22, 2003. The referenced applications and their teachings are incorporated herein by reference in their entirety.

GOVERNMENT FUNDING

This invention was made with government support under Grant No. GM020919 awarded by the National Institutes of Health. The government has certain rights in the Invention.

BACKGROUND OF THE INVENTION

Experimental animals serve as useful models for studying human diseases. Advances in transgenic and targeted mutation technology have made the mouse not only a successful surrogate organism for human genome analysis, but also the most valuable model system to investigate the genetics and pathogenesis of human diseases. The valid interpretation of experimental results obtained from mouse studies depends upon the assurance that the mouse models used are genetically pure and well defined. For this reason, researchers have traditionally used inbred strains for experiments, because these mice, in contrast to outbred mouse stocks, offer uniformity and constancy of genotypes. Mice of inbred strains can be repeatedly accessed as homogeneous experimental individuals, with predictable phenotypes and defined allelic composition.

The constancy of genotype in inbred strain mice, however, is never fully realized because both new mutations arise and gradually accumulate together with continual allele fixation of residual heterozygosity. These changes in genotype within inbred mice are known as genetic drift. At each generation, there is a likelihood of spontaneous new mutations arising. These mutations first occur as heterozygous mutations. When both founders of an inbred strain, by chance, become homozygous for a spontaneous mutation, this mutation becomes fixed in the inbred strain, and all later generations of this inbred mouse strain will carry this mutation.

Genetic drift as a result of the rise of spontaneous mutations will impact genetic analysis performed on animals derived from an inbred strain. The valid interpretation of experimental data generated using inbred animals is undermined by genetic drift. A recent publication illustrates this point. In 2001, Specht and Schoepfer discovered a chromosomal deletion in C57BL/6JO1aHsd mice (See Specht and Schoepfer, Deletion of the alpha-synuclein locus in a subpopulation of C57BL/6J inbred mice, BMC Neurosci. 2, 11 (2001). The mutation was the ablation of the more than 79 kb of the alpha-synuclein locus. This gene encodes a presynaptic telencephalic protein that has been implicated in the etiology of Parkinson and Alzheimer diseases. Many researchers have used C57BL/6JO1aHsd mice as a wild-type control for their experiments or to backcross with other mutations, unaware of this problem. Now their experimental results need to be re-evaluated in light of the alpha-synuclein deletion present in the strain. See Wotjak, C57BLack/BOX? The importance of exact mouse strain nomenclature, Trends in Genetics 19: 183-184 (2003).

Moreover, researchers frequently need to compare data obtained from inbred animals over extended periods of time. Due to the effects of genetic drift, over time, inbred strain mice become genetically different from the "same" inbred mice at an earlier point in time. The longer the time span, the more likely genetic differences will accumulate and become fixed. The existence of genetic drift thus undermines one's ability to carry out valid comparisons across extended periods of time.

For these reasons it is desirable to reduce genetic drift in inbred animal strains and maintain their genetic stability over protracted periods of time. There is a pressing need in the art for methods of maintaining genetic stability of inbred animal strains. Such methods are provided herein.

SUMMARY OF THE INVENTION

The present invention provides novel methods of maintaining genetic stability of inbred rodent strains, such as inbred mouse strains. Currently, a pedigreed foundation colony is maintained for an inbred mouse strain. The foundation colony of an inbred mouse strain is derived from a single brother-sister mating. Two to four times a year, a new brother-sister pair is selected from the foundation colony as the new founder pair to re-establish the colony. Using this approach, a foundation colony today will be genetically different from the foundation colony years from now, because of the accumulation of spontaneous mutations and allele fixation in the inbred mouse strain over time.

Applicants have devised novel methods of limiting genetic drift and maintaining genetic stability of inbred mice by producing a pedigree-tracked stock of cryopreserved embryos, gametes or pre-gametes derived from a foundation colony and using the stock to re-establish the foundation colony at appropriate intervals. Use of a cryopreserved stock of embryo, gametes or pre-gametes as a repository for the foundation colony and periodically re-establishing the foundation colony using the cryopreserved stock makes it possible to reduce the numbers of generations passed in a given time period and thus effectively reduce the effective rate of genetic drift. Because the pedigree of each embryo, gamete or pre-gamete in the stock is known, one can selectively recover embryos, gametes or pre-gametes that are obtained only from brother-sister or only from parent-offspring pairs. As a result, the inbred mouse strain is propagated through consecutive brother-sister or parent-offspring breeding, keeping the inbred status of the mouse strain intact. This process can be repeated at appropriate intervals, thus allowing one to maintain an inbred mouse strain with limited genetic drift without affecting the inbred status of the strain. It will become evident that it is not necessary that all embryos, gametes, pre-gametes be cryopreserved before being used in the methods described herein. Embryos, gametes and pre-gametes can be collected. A portion of these can be used as freshly obtained embryos, gametes or pre-gametes (without cryopreservation) and a portion reserved for later use, such as to produce pedigree-tracked cryopreserved stock, as described herein. The methods described herein refer to cryopreserved stock and other cryopreserved materials. It is understood that "cryopreserved" is used for purposes of illustration only and that vitrified, freeze-dried, frozen or otherwise appropriately preserved stocks and other appropriately preserved materials can also be used (substituted) in the methods.

A pedigree-tracked stock of cryopreserved embryos is produced by obtaining and cryopreserving embryos from a brother-sister pair derived from a foundation colony. Embryos may be obtained by breeding the brother-sister pairs or parent-offspring pairs. Embryo production may be by mating (copulation) or by in vitro or in vivo artificial means. Artificial means include, but are not limited to, assisted reproductive techniques, such as artificial insemination, in vitro fertilization of in vitro or in vivo matured oocytes, intracytoplasmic sperm injection and cloning.

The pedigree-tracked cryopreserved stock may also be a stock of embryonic stem cells, a stock of gametes, or a stock of pre-gametes. Gametes, pre-gametes or embryonic stem cells are derived from a foundation colony of inbred mouse strain. Such cryopreserved stocks can be used as frozen repositories for a foundation colony to maintain genetic stability of an inbred strain. The present invention provides methods of producing pedigree-tracked cryopreserved stock and methods of using the stock to maintain genetic stability of an inbred rodent (e.g., mouse, rat) strain.

The present invention also provides pedigree-tracked stocks of cryopreserved non-human animal (inbred rodent) embryos, gametes, pre-gametes, or embryonic stem cells. These are referred to herein, respectively, as pedigree-tracked cryopreserved embryo stock; pedigree-tracked cryopreserved gamete stock; and pedigree-tracked cryopreserved pre-gamete stock. Each is an example of a foundation stock, which is a stock of reproductive cells that can be used to produce a new founder pair. Reproductive cells include male and female pre-gametes, gametes, reproductive organs (e.g., ovaries and ovary fragments) and embryos. A foundation stock can include only one type of reproductive cells (e.g., only male gametes or only female gametes) or a mixture of such cells (e.g., male gametes and pre-gametes or female gametes and pre-gametes). In those instances in which a foundation stock includes reproductive cells (e.g., sperm) from only one gender, use of a stock of reproductive cells (e.g., oocytes) of the other gender must also be used. Each of these stocks is derived from a foundation colony of an inbred rodent (e.g., mouse, rat) strain. The pedigree of the respective embryos, gametes, pre-gametes or embryonic stem cells for each strain is tracked and recorded to permit selective recovery at a future time.

Applicants further provide genetically stabilized non-human animal inbred strains (e.g., inbred rodent strains) that are produced by the methods described herein. A non-human animal may be a rodent, such as a rat or a mouse.

Applicants further provide methods for conducting a business of supplying genetically stabilized non-human animal inbred strains, such as inbred rodent strains (e.g., inbred mouse or rat strains). A foundation colony is maintained for an inbred strain and a pedigree-tracked cryopreserved stock of embryos derived from the foundation colony is produced. At appropriate intervals, a pair of brother-sister embryos derived from a single brother-sister pair is selected and live animals are produced from the sibling embryos. A brother-sister pair is selected from the animals produced and is used as a new founder pair to re-establish the foundation stock. In response to a customer's request, one or multiple animals of the genetically stabilized inbred mouse strain are supplied to the customer.

Practice of these methods makes it possible to maintain an inbred strain with limited genetic drift without affecting the inbred status of the strain. As a result, inbred animals that are truly genetically uniform with well-defined genotypes over an extended period of time will be available to animal researchers, greatly aiding valid data interpretation and meaningful data comparison.

BRIEF DESCRIPTION OF THE DRAWINGS

FIG. 1 shows a scheme to generate sufficient numbers of pedigree-tracked embryos derived from a foundation colony to produce pedigree-tracked cryopreserved embryos for maintaining genetic stability of an inbred strain.

FIG. 2 is a bar graph that shows the number of oocytes that were isolated and the fertilization rates after serial transfer of fresh BALB/cByJ ovaries.

FIG. 3 is a bar graph that shows the number of oocytes that were isolated and the fertilization rates after serial transfer of frozen BALB/cByJ ovaries.

FIG. 4 is a bar graph that shows the number of oocytes that were isolated after serial ovary transplantation of fresh C57BL/6J ovaries.

FIG. 5 is a bar graph which shows the fertilization rates after serial ovary transplantation of fresh C57BL/6J ovaries.

FIG. 6 shows ovaries from BALB/cByJ complete (left panel) and divided into 16 fragments.

FIG. 7 shows ovaries from BALB/cByJ complete (top) and divided into 32 fragments.

DETAILED DESCRIPTION OF THE INVENTION

The present invention provides novel methods of maintaining genetic stability of non-human animal inbred strains, such as inbred rodent strains, including inbred mouse strains and inbred rat strains. As described herein, the genetic stability of an inbred animal strain is maintained by producing pedigree-tracked cryopreserved embryos, gametes or pre-gametes derived from a foundation colony and using these to re-establish the foundation colony at appropriate intervals. Practice of the methods reduces the numbers of generations passed for a given time period and thus reduces the risk of genetic drift. Because the pedigree of each cryopreserved embryo, gamete or pre-gamete is known, one can selectively recover embryos, gametes or pre-gametes that are obtained only from either brother-sister or only from parent-offspring. The inbred strain (such as an inbred mouse strain) is propagated through consecutive brother-sister or parent-offspring breeding, keeping the inbred status of the strain intact.

I. Maintaining Genetic Stability Using Cryopreserved Embryos:

The present invention provides methods of maintaining genetic stability of a non-human animal inbred strain. In one embodiment, the method comprises: (1) maintaining a foundation colony of an inbred strain; (2) producing pedigree-tracked stock of cryopreserved embryos derived from the foundation colony; (3) at appropriate intervals, selecting cryopreserved embryos that are inbred breeding pairs, and producing live animals from the embryos; (4) selecting an inbred breeding pair from the animals produced, and using the pair as a new founder pair to produce animals; and (5) repeating steps (3) to (4) at appropriate intervals. In this manner, genetic drift of the inbred mouse strain is minimized and genetic stability of the strain is effectively maintained The term "genetic stability" as used herein, refers to effectively reduced genetic drift in an inbred strain, as compared to the genetic drift that would occur if the inbred strain is maintained using currently available methods. The effective reduction of genetic drift means reduced genotypic changes in an inbred strain. Depending on where the changes occur in the genome, the genetic changes may or may not lead to phenotypic changes. For example, a mutation in the non-coding region of the genome will likely result in no change in the phenotype of an animal. A mutation that occurs in the foundation stock of a strain maintained under the Genetic Stability program will not persist in the strain; it will be purged from the entire animal colony because cryopreserved embryos are thawed and used as new foundation stock. Genetic drift may be assessed by examining a variety of indices, including, for example, coat color, biochemical and immunological markers isoenzymes, major histocompatibility complex (MHC), erythrocytic antigens, hemolytic complement (Hc—formerly C5), tail skin grafting, and behavior changes. Genetic drift may also be assessed by examining a variety of molecular markers using any of techniques available in the art, including, for example, two dimensional protein gels, PCR, SNPs, gene expression profiling, and sequencing. Genetic drift may also be assessed by examining a variety of proteomic markers, using techniques available in the art, such as mass spectrometry, liquid chromatography mass spectrometry (LC/MS or LC-MS) two-dimensional differential in-gel electrophoresis, protein microarray, Western blot, immunohistochemical staining, enzyme linked immunosorbent assay (ELISA), immunoassays and flow cytometry.

An inbred strain is produced by a managed breeding scheme that leads to a reduction in heterozygosity. Acceptable breeding schemes include: parent-offspring breeding and brother-sister breeding. An inbred strain is typically produced by breeding brother with sister for 10 or more consecutive generations Animals in the $10^{th}$ or a subsequent generation of an inbred strain can be traced to a single ancestral breeding pair. In one embodiment, an inbred strain is produced by breeding brother with sister for 20 or more consecutive generations; animals in the $20^{th}$ or a subsequent generation can be traced to a single ancestral breeding pair.

The term "inbred breeding pair", as used herein, refers to any breeding pair whose breeding leads to reduced heterozygosity. An inbred breeding pair may be a parent-offspring pair or a brother-sister pair. In one embodiment, the inbred breeding pair is a brother-sister pair. Brother-sister pair will be used as illustration throughout the application to describe the present invention. However, a person of ordinary skill in the art will recognize that a parent-offspring pair may be substituted for the brother-sister pair in the present application.

a. Maintaining a Foundation Colony of an Inbred Strain

The foundation colony of an inbred mouse strain is maintained using techniques known to one skilled in the art. As used herein, the term "foundation colony" refers to a colony from which all subsequent animals of the strain are derived. A founder pair is an inbred breeding pair, that gives rise to all subsequent animals for a particular strain. A foundation colony can include a single founder pair or more than one founder pair. Founders are selected from the foundation colony.

In specific embodiments, a non-human animal preferably is a rodent, such as a rat or a mouse. A non-human animal may also be a hamster, a guinea pig, a horse, a pig, a goat, a sheep, a chicken, a turkey, a primate or any other non-human animal for which an inbred strain is maintained.

Inbred mouse strains include, but are not limited to 129S1, 129T2, 129X1, 129P3, 129P1, A, AKR, BALB/c, C3H, C57BL/10, C57BL/6, C57BLKS, C57BR/cd, C57L, CAST/Ei, CBA, DBA/1, DBA/2, FVB, MRL, NOD, SJL, MOLF/Ei, SWR, NOR, NZB, NZW, RBF, BUB, I, LP, NON, P, PL, RIIS, SM, C58, ALR, ALS, BPH, BPL, BPN, DDY, EL, KK, LG, MA, NH, NZM2410, NZO, RF, SB, SEA, SI, SOD1, SPRET/Ei, WSB/Ei, YBR, and all inbred substrains of each of these mouse strains. Accepted mouse strain nomenclature usage requires that each strain is further identified by the addition of a Lab Code at the end of the strain code. The current list of Lab Codes is maintained by the Institute for Laboratory Animal Research which maintains the International Laboratory Code Registry and can be accessed at: dels.nas.edu/ilar/codes.asp The term "substrains," as used herein, refers to colonies within the same strain, such as the same mouse strain, that are genetically different from each other. A substrain may arise where two colonies of the same inbred strain have been separated for more than 10 generations, or it may arise where there is known genetic difference between separate colonies of the same strain. The genetic difference between different substrains may also be a result of residual heterozygosity in the ancestors at the time of separation which becomes fixed, and/or a result of spontaneous mutation during subsequent generations (genetic drift). Examples of substrains include, but are not limited to, 129S1/SvImJ, 129T2/SvEmsJ, 129X1/SvJ, 129P3/J, A/J, AKR/J, BALB/cByJ, BALB/cJ, BTBR T+ tf/J, BUB/BnJ, C3H/HeJ, C3H/HeOuJ, C3HeB/FeJ, C57BL/10J, C57BL/6J, C57BL/6NJ, C57BLKS/J, C57L/J, C58/J, C57BR/cdJ, CBA/CaHN-Btkxid/J, CBA/J, DBA/1J, CAST/EiJ, DBA/1LacJ, DBA/2J, DDY/Jc1SidSeyFrkJ, FVB/NJ, KK/H1J, MRL/MpJ, MOLF/EiJ, NONcNZO10/LtJ, NON/ShiLtJ, NOD/ShiLtJ, NZL/LtJ, PL/J, SM/J, SJL/J, SWR/J, NOR/LtJ, NZB/B1NJ, NZW/LacJ, PWD/PhJ, RBF/DnJ, WSB/EiJ, 129S6/SvEvTac, AJTAC, BALB/cAnNTac, BALB/cJBomTac, BALB/cABomTac, C57BL/6NTac, C57BL/6JBomTac, C57BL/10SgAiTac, C3H/HeNTac, CBA/JBomTac, DBA/1JBomTac, DBA/2NTac, DBA/2JBomTac, FVB/NTac, NOD/MrkTac, NZM/AegTac, SJL/JcrNTac, BALB/cAnNCr1BR, C3H/HeNCr1BR, C57BL/6NCr1BR, DBA/2NCr1BR, FVB/NCr1BR, C.B-17/IcrCr1BR, 129/SvPasIcoCr1BR, SJL/Jor1IcoCr1BR, A/Jo1aHsd, BALB/cAnNHsd, C3H/HeNHsd, C57BL/10Sc-NHsd, C57BL/6NHsd, CBA/JCrHsd, DBA/2NHsd, FVB/NHsd, SAMP1/KaHsd, SAMP6/TaHsd, SAMP8/TaHsd, SAMP10/TaHsd, SJL/JCrHsd, AKR/O1aHsd, BiozziABII/RijIIsd, C57BL/6JO1aHsd, FVB/NhanIIsd, MRL/MpO1aIIsd, NZB/O1aIIsd, NZW/O1aHsd, SWR/O1aHsd, 129P2/O1aHsd, and 129S2/SvHsd.

Inbred mouse strains also include all strains produced by any transgenic, knockout or siRNA (small interference RNA) technique or other genetic manipulation technologies that have been bred brother with sister or parent-offspring for ten or more consecutive generations.

Inbred rat strains include, but are not limited to, AAW, AB, ACI, ALB, AO, BB, BDE, BDI, BDIX, BDX, BLK, BN (Brown Norway) BUF (Buffalo), COP (Copenhagen), DA, F344 (Fisher), FCH, FH, FHH, GK, MR, LE (Long Evans), LEW (Lewis), LOU, LUDW, PVG, ZDF, SD (Sprague-Dawley), SHR, SHROB, SS WAG, WF, WIST, WKY, WKYO, PCK, Fisher CDF, SHRSP/A3NCr1 (Stroke Prone Rat) (see www.informatics.jax.org/external/festing/rat/STRAINS.shtml)

b. Producing a Pedigree-Tracked Stock of Cryopreserved Embryos

One embodiment relates to methods of producing a pedigree-tracked stock of cryopreserved animal embryos derived from a foundation colony, as described herein.

A pedigree-tracked stock is a stock in which the pedigree of each embryo in the stock is known. Pedigrees of the embryos may be tracked by following the family tree of the embryos and recording the family tree information. For example, each embryo may be separately labeled with its pedigree information. Alternatively, sibling embryos may be physically stored and labeled together. The term "sibling embryos" as used herein, refers to embryos that are derived from breeding a single brother-sister or parent-offspring pair (or an inbred breeding pair). The cryopreserved embryos may be stored by methods known to those skilled in the art. In one embodiment, cryopreserved embryos are stored in sterile plastic insemination straws. Each straw contains only sibling embryos. A straw may contain one embryo only or it may contain multiple sibling embryos. Alternatively, cryopreserved embryos may be stored in other appropriate containers, such as plastic vials or glass ampoules.

Embryos of the pedigree-tracked stock may be any stage embryos that can be successfully cryopreserved and recovered to produce live animals. Such embryos include all stages of preimplantation embryos from zygotes to blastocysts. Thus, the embryo may be, for example, a one-cell embryo (a zygote), a two-cell embryo, a four-cell embryo, an eight-cell embryo, a morula or a blastocyst. A morula is a spherical mass of cells resulting from cleavage of a one cell embryo; the blastocyst develops from the morula and has a blastocoel and an asymmetrically placed cluster of cells, the inner cell mass.

The term "cryopreserved" as used herein refers to being preserved by using a process of cooling to low-subzero Celsius temperatures. The cells, embryos, gametes or pre-gametes of the invention are frozen at temperatures generally lower than 0° C. For example, −80° C. can be used for short term storage, and from −130 ° C. to −196 ° C. or lower can be used for long term storage. Cells, embryos, gametes or pre-gametes can be cryopreserved for an indefinite length of time. Methods and tools for cryopreservation are well-known to those skilled in the art. See, e.g., U.S. Pat. No. 5,160,312, entitled "Cryopreservation Process for Direct Transfer of Embryos", Glenister and Hall, "Cryopreservation and rederivation of embryos and gametes", in Mouse Genetics & Transgenics: A Practical Approach, $2^{nd}$ Edition (I Jackson & C Abbott, eds.) Oxford Univ. Press, Oxford, pp. 27-29. Methods known to those in the field, such as vitrification (Nakao K, Nakagata N, Katsuki M., Simple and efficient vitrification procedure for cryopreservation of mouse embryos. Exp Anim 1997 July; 46(3):231-4; Nakagata N. High survival rate of unfertilized mouse oocytes after vitrification, J Reprod Fertil. 1989 November; 87(2):479-83; dela Peña E C, Takahashi Y, Katagiri S, Atabay E C, Nagano M. Birth of pups after transfer of mouse embryos derived from vitrified preantral follicles. Reproduction. 2002, 123(4):593-600).

Freeze drying, also know as lyophilization or cryodesiccation, is a dehydration process to preserve cells, pre-gametes or gametes by freezing and lowering the pressure to sublimate water. Freeze-drying machines may be used. Cryoprotectants (for example sugars) may be added during the freeze drying process. For freeze-drying cells, pre-gametes or gametes may be diluted in buffer or media (T. Wakayara and R. Yanagimachi, *Nature Biotechnol.* 16, 639 (1998); Kawase Y, Araya H, Kamada N, Jishage K, Suzuki H., Possibility of long-term preservation of freeze-dried mouse spermatozoa. Biol Reprod. 2005 March; 72(3):568-73; Ono T, Mizutani E, Li C, Wakayama T, Nuclear transfer preserves the nuclear genome of freeze-dried mouse cells, J Reprod Dev. 2008 December; 54(6):486-91; U.S. patent application Ser. No. 11/811,968, US 2008/0026361). Freeze-dried cells, gametes or pre-gametes can be stored at ambient (room) temperature or temperatures such as 4° C., −20° C., −80° C., −136° C., −196° C. For longer storage, lower temperatures, such as −20° C., −80° C., −136° C., −196° C. are preferred.

"Embryos derived from a foundation colony" as used herein, includes embryos obtained directly from a founder pair and embryos obtained from progeny of the founder pair.

The number of embryos or gametes needed in a cryopreserved stock depends on many factors, including, for example, the length of time over which a genetic stability program is to be maintained, the frequency with which the cryopreserved stock is used to re-establish a foundation colony, and the efficiency of producing live animals from cryopreserved embryos. These factors will differ among different animal species and among different strains of the same animal species. For example, mice from different inbred strains are known to vary in the recovery efficiency of cryopreserved embryos or gametes.

The number of female animals needed to produce a desired number of embryos will also vary. The number of females needed is inversely correlated with the number of oocytes that can be obtained from each female, the proportion of oocytes that are fertilized and the proportion of embryos that develop to term following embryo transfer. Therefore, the number of females required is a function of the efficiency of each step. High efficiency at each step reduces the total number of females required.

In one embodiment, a pedigree-tracked stock of cryopreserved embryos may be produced by first obtaining embryos from a brother-sister pair (founder pair) of the foundation colony and then cryopreserving the embryos. Pedigree information is tracked and recorded such that each cryopreserved embryo has an identifiable pedigree. In this embodiment, embryos are produced directly by breeding a founder pair. As a result, the pedigree-tracked stock includes only sibling embryos.

Alternatively, the foundation colony is first expanded to produce sufficient numbers of brother-sister pairs. Thus, in another embodiment, a pedigree-tracked stock of cryopreserved embryos derived from a foundation colony may be produced by: (1) obtaining progeny from the foundation colony such that the progeny comprises appropriate numbers of brother-sister pairs; (2) producing embryos from brother-sister pairs selected from progeny obtained in (1); and (3) cryopreserving embryos produced in (2). Pedigree information is tracked and recorded such that each cryopreserved embryo has an identifiable pedigree. The pedigree-tracked stock produced in this embodiment comprises embryos derived from breeding more than one brother-sister pairs.

One brother-sister pair is distinct from another pair if either the male or the female is different between the two pairs. For example, the brother-sister pair male A and female B is different from the brother-sister pair male A and female C, and from the brother-sister pair male D and female B. "Progeny" as used herein, refers to generations of animals derived from a founder pair, including, for example, F1, F2, F3 and F4 generations. "Appropriate number of distinct brother-sister pairs" or "appropriate number of parent-offspring pairs" is a number that will generate sufficient numbers of embryos for the purpose of creating a cryopreserved stock to maintain genetic stability of an inbred strain.

Obtaining progeny from a foundation stock may be achieved by breeding techniques known to those skilled in the art, including, for example, natural mating, artificial insemination and in vitro fertilization.

Embryos may be obtained from breeding the brother-sister founder pair. "Breeding" as used herein, means the union of male and female gametes so that fertilization occurs. Such a union may be brought about by mating (copulation) or by in vitro or in vivo artificial means. Artificial means include, but are not limited to, artificial insemination, in vitro fertilization, intracytoplasmic sperm injection, electrofusion and cloning. Any method to produce properly aged embryos may be used.

Artificial insemination is a process of fertilizing female animals by manual injection or application of sperm. In such a procedure, male animals are not required at the time of insemination; sperm obtained from the animals can be used. See Wolfe, 1967, and Sato and Kumura, 2002. When breeding is achieved by natural mating or artificial insemination, embryos may be obtained by flushing the oviduct or uterus of the female after the mating or artificial insemination. See Hogan et al., 2003. The embryo splitting technique is well known to those skilled in the art. Embryo splitting can be carried out by, for example, dividing normal embryos (from 2 cell to morula stage) with a micromanipulator or similar procedure.

In vitro fertilization (IVF) is also well known in the art. See, for example, Hogan et al., Manipulating the Mouse Embryos, A Laboratory Manual, $2^{nd}$ Ed. Page 146-147 (1994). IVF generally comprises collecting oocytes and sperm from a female and a male respectively, fertilizing oocytes from the female with sperm from the male and maintaining the resulting fertilized oocytes under suitable conditions for development of the fertilized oocytes into embryos. Embryos may be harvested at different stages. The female may be superovulated before oocytes are collected for IVF. See, for example, Hogan et al., 2003. As described herein, the oocytes and the sperm are obtained from a brother-sister pair. IVF can be a useful tool to increase the numbers of embryos obtained from a single female.

Intracytoplasmic sperm injection (ICSI) may be used to improve fertilization rates or to achieve fertilization. The ICSI procedure involves removal of the cumulus cells surrounding oocytes and injection of the sperm or haploid spermatids into the oocytes, ordinarily through a glass pipette. Kimura Y, Yanagimachi R., Development of normal mice from oocytes injected with secondary spermatocyte nuclei., Biol Reprod. 1995 October; 53(4):855-62. Spermatids, spermatogonial stem cells and male germ cells can be differentiated in vitro and then used for ICSI (Marh J, Tres L L, Yamazaki Y, Yanagimachi R, Kierszenbaum A L., Mouse round spermatids developed in vitro from preexisting spermatocytes can produce normal offspring by nuclear injection into in vivo-developed mature oocytes. Biol Reprod. 2003 July; 69(1):169-76. Movahedin M, Ajeen A, Ghorbanzadeh N, Tiraihi T, Valojerdi M R, Kazemnejad A., In vitro maturation of fresh and frozen-thawed mouse round spermatids. Andrologia. 2004 October; 36(5):269-76. Ogura A, Matsuda J, Asano T, Suzuki O, Yanagimachi R., Mouse oocytes injected with cryopreserved round spermatids can develop into normal offspring. J Assist Reprod Genet. 1996 May; 13(5):431-4. Shinohara T, Inoue K, Ogonuki N, Kanatsu-Shinohara M, Mild H, Nakata K, Kurome M, Nagashima H, Toyokuni S, Kogishi K, Honjo T, Ogura A., Birth of offspring following transplantation of cryopreserved immature testicular pieces and in-vitro microinsemination. Hum Reprod. 2002 December; 17(12):3039-45. Chuma S, Kanatsu-Shinohara M, Inoue K, Ogonuki N, Miki H, Toyokuni S, Hosokawa M, Nakatsuji N, Ogura A, Shinohara T., Spermatogenesis from epiblast and primordial germ cells following transplantation into postnatal mouse testis. Development. 2005 January;132 (1):117-22).

As an alternative to collecting mature oocytes for IVF from a female, immature oocytes may be obtained and allowed to mature in vitro, a technique known as "in vitro maturation". As an alternative, follicles, e.g., primary follicle or germ cells, may be isolated from the female and cultured in vitro to obtain oocytes useful for fertilization. In mammals, only a small fraction of immature oocytes develop into mature oocytes; the rest degenerate and die. By isolating immature oocytes from animals and allowing them to mature in vitro, one can obtain many more oocytes suitable for IVF from a given female. Mammalian oocytes are known to undergo maturation in vitro. In the case of mice, cattle and other mammals, in vitro matured oocytes have been fertilized in vitro and given rise to normal healthy offspring when embryos were transferred to an appropriate uterus (Schroeder and Eppig 1984 Dev. Biol. 102:493; Sirard et al. 1988, Biol. Reprod. 39:546). In vitro maturation technique is well known in the art. See, for example, Chiu et al., Effects of Myo-inositol on the in-vitro Maturation and Subsequent Development of Mouse Oocytes, Human Reprod. 18: 408-416 (2003) and O'Brien et al., A Revised Protocol for In Vitro Development of Mouse Oocytes from Primordial Follicles Dramatically Improves Their Developmental Competence, Biol. Reprod. 68: 1682-1686 (2003).

In another alternative, oocytes may be collected from a "host" female into whom a section or fragment of an ovary or ovaries from a desired female had previously been implanted. The terms section of and fragment of an ovary/ovaries are used interchangeably herein. The desired female is the female from a brother-sister pair derived from the foundation colony, from whom oocytes are needed for IVF. This is achieved by harvesting ovaries from the female of a brother-sister pair, sub-dividing the ovaries into fragments or sections, implanting at least one fragment or section into a host female ovariectomized by surgery or into a chemically or genetically compromised host female and collecting oocytes from each of the host females. This approach results in more oocytes obtained for a given female.

Other methods that can be used include surgical oocyte retrieval, ovary transfer, ovary splitting, ovary fragment transfer, in vitro maturation of oocytes, follicles, spermatogonial stem cells, in vitro differentiation of germ cells, and in vitro differentiation of primordial cells.

Host Recipients for Pre-Gamete Transplantation

A variety of female host rodents (e.g., mouse or rat female, are suitable for receiving ovarian transplants (ovary or ovary fragments or ovary sections). Typically, a female host (e.g., mouse, rat) is a histocompatible female (e.g., female mouse, female rat) who lacks ovaries, has had its ovaries removed (e.g. surgically, by ovariectomy or by cell-ablation techniques) or has depleted ovary function. For example, the ovary function can be destroyed by chemotherapy, such as by intraperitoneal injection of butane-1,4-diyl dimethanesulfonate, also known as busulfan or busulphan (e.g., at concentrations from 10-30 mg/kg body weight); intraperitoneal injection of a combination of busulfan (10-30 mg/kg body weight) with cyclophosphamide (N,N-bis(2-chloroethyl)-1, 3,2-oxazaphosphinan-2-amine 2-oxide), also known as cytophosphane (120 mg/kg body weight); or intraperitoneal injection of 9,10-dimethylbenz[a]anthracene (DMBA) (e.g. 80 mg/kg body weight). Alternatively, the host female can be injected repeatedly with 4-vinylcyclohexene (VCH) or 4-vinylcyclohexene diepoxide (VCD), such as at a concentration of from 60 mg/kg to 160 mg/kg injected intraperitoneal over 8 to 21 days, which results in destruction of primordial and primary ovarian follicles in rat and mouse (Flaws, J. A., Doerr, J. K., Sipes, I. G., and Hoyer, P. B. (1994). Destruction of pre-antral follicles in adult rats by 4-vinylcyclohexene diepoxide. Reprod. Toxicol. 8, 509-514; Smith, B. J., Carter, D. E., and Sipes, I. G. (1990a). Comparison of the disposition and in vitro metabolism of 4-vinylcyclohexene in the female mouse and rat. Toxicol. Appl. Pharmacol. 105, 364-371). Ovary function may also be depleted by radiation or injection of cytotoxic substances, or other suitable methods known in the art.

Alternatively, the female host can be a sterile female rodent (female mouse, female rat), such as any of the following mouse strains: WBB6F1/J-KitW/KitW-v/J (The Jackson Laboratory stock number 100410), or a genetically engineered rodent that is sterile, (e.g., luteinizing hormone receptor-knockout (LuRKO) mice (Pakarainen et al. 2005, J Clin Invest. 115(7): 1862-1868) or C/EBP-beta (CCAAT/enhancer-binding protein beta) knockout mice (Sterneck et al. 1997, Genes and Dev. 11, 2153-2162)).

Pre-gametes may be matured into gametes in vitro or in vivo. A variety of female host rodents (e.g., mice, rats) is suitable for receiving pre-gametes. Typically, a female host rodent (e.g., mouse, rat) is histocompatible and has depleted ovary function. For example, the ovary function can be destroyed by chemotherapy, such as by intraperitoneal injection of an alkylating agent, butane-1,4-diyl dimethanesulfonate, also known as busulfan or busulphan (at concentrations from 10-30 mg/kg body weight) (J. Johnson, et al. 2004, Nature 428, 145-150); intraperitoneal injection of combination of busulfan (10-30 mg/kg body weight) with cyclophosphamide (N,N-bis(2-chloroethyl)-1,3,2-oxazaphosphinan-2-amine 2-oxide), also known as cytophosphane (120 mg/kg body weight) (Zou et al., Production of offspring from a germline stem cell line derived from neonatal ovaries; 2009, Nature Cell Biology 11, 631-636; K. Shiromizu, S. S. Thorgeirsson and D. R. Mattison, Effect of cyclophosphamide on oocyte and follicle number in Sprague-Dawley rats, C57BL/6N and DBA/2N mice, Pediatr. Pharmacol. 4 (1984), pp. 213-221); intraperitoneal injection of 9,10-dimethylbenz[a]anthracene (DMBA) (e.g. 80 mg/kg body weight) (J. Johnson, et al. 2004, Nature 428, 145-150). Alternatively, a host female can be injected repeatedly with 4-vinylcyclohexene (VCH) or 4-vinylcyclohexene diepoxide (VCD), such as at a concentration of from 60 mg/kg to 160 mg/kg injected intraperitoneally over 8 to 21 days, which results in destruction of primordial and primary ovarian follicles in rat and mouse (Flaws, J. A., Doerr, J. K., Sipes, I. G., and Hoyer, P. B. (1994). Destruction of pre-antral follicles in adult rats by 4-vinylcyclohexene diepoxide. Reprod. Toxicol. 8, 509-514; Smith, B. J., Carter, D. E., and Sipes, I. G. (1990a). Comparison of the disposition and in vitro metabolism of 4-vinylcyclohexene in the female mouse and rat. Toxicol. Appl. Pharmacol. 105, 364-371). Ovary function may also be depleted by radiation or injection of cytotoxic substances, or other suitable methods known in the art.

Alternatively, the female host rodent can be a sterile female rodent (e.g., mouse, rat) such as any of the following mouse strains: WBB6F1/J-KitW/KitW-v/J (The Jackson Laboratory stock number 100410), or a genetically engineered rodent that is sterile, (e.g., luteinizing hormone receptor-knockout (LuRKO) mice (Pakarainen et al. 2005, J Clin Invest. 115(7): 1862-1868) or C/EBP-beta (CCAAT/enhancer-binding protein beta) knockout mice (Sterneck et al. 1997, Genes and Dev. 11, 2153-2162)).

A variety of male host rodents is suitable for receiving male pre-gametes for maturation. Typically, a male host rodent (mouse, rat) is histocompatible and has a depleted male germ cell lineage function. Such hosts can be generated by chemotherapy, for example by nonlethal intraperitoneal injection of an alkylating agent, e.g. butane-1,4-diyl dimethanesulfonate, also known as busulfan or busulphan (e.g. 40-60 mg/kg body weight) (Shinohara et al. 2002, Biol Reprod 66:1491-1497; Brinster et al. 2003, Biol. Reprod. 69, 412-420), by local radiation treatment (Creemers et al. 2002, Biol Reprod 66, 1597-1584; Zhang et al. 2006, J Androl 27 (3), 365-375; Zhang et al. 2007, Journal of Cellular Physiology, 211, 149-158), or by administration of cytotoxic substances, surgical ablation (including laser surgery) or testicular cooling. Male host rodents can be genetically engineered. Spontaneous mutant mice can be used as recipient; for example the dominant white spotting (W) homozygous mutant male mouse, carrying a mutation in the c-kit receptor tyrosine kinase can be used. Mouse strains with mutations in the c-kit receptor tyrosine kinase are for example Wv/W54 (Brinster R. L., Avarcbock M. R. Proc. Natl. Acad. Sci. USA. 1994; 91:11303-11307); W/Wv; KitW/KitW-v, WBB6F1/J-KitW/KitW-v/J (The Jackson Laboratory stock number 100410); KitW-v (The Jackson Laboratory stock number 49); KitW (The Jackson Laboratory stock number 692). Other suitable mouse strains may be Kit1S1/Kit1S1-d (The Jackson Laboratory stock number 100401) and juvenile spermatogonial depletion (jsd) mutant mice (C57BL/6J-Utp14bjsd/J, The Jackson Laboratory Stock number 708).

c. Producing Live Animals from Cryopreserved Embryo Stock

At an appropriate time, cryopreserved sibling embryos are selected and live animals are produced from these sibling embryos. In one embodiment, live animals are produced from one set of sibling embryos. In another embodiment, live animals are produced from more than one set of sibling embryos. Sibling embryos are those produced from the same male and female.

Producing live animals from cryopreserved embryos may be carried out using techniques known to those skilled in the art. In one embodiment, live animals are produced from cryopreserved embryos by: (1) thawing the cryopreserved embryos; (2) implanting the thawed embryos into at least one pseudopregnant female recipient; and (3) maintaining the pseudopregnant female recipients under conditions suitable for production of live animals. As a result, live animals are produced. In some embodiments, transfer techniques known to one of skill in the art, such as embryo transfer, embryo splitting and in vitro culture of fertilized oocytes are used to increase the number of live born animals.

The term "thawing" as used herein refers to the process of increasing the temperature of cryopreserved materials. Methods of thawing cryopreserved materials, such that they are able to give rise to live animals after the thawing process, are well-known to those of ordinary skill in the art.

The term "reconstitution" as used herein refers to the process of rehydration of freeze-dried materials. Methods of rehydrating freeze-dried materials, such as cells, gametes or pre-gametes, are well known to those of ordinary skill in the art, and include for example adding water, media or buffer to the freeze-dried materials. For example rehydrated sperm can be used for intracytoplasmic sperm injection (ICSI) into oocytes.

The term "implanting" as used herein in reference to embryos, refers to the transfer of one or more embryos to a female animal with an embryo as described herein. A pseudopregnant female recipient is a female animal whose reproductive tract becomes receptive for transferred embryos. A pseudopregnant female animal is generated, for example, by mating a female with a sterile male. The technique of implanting a pseudopregnant female is well known to a person of ordinary skill in the art. See, e.g., Recovery, Culture and Transfer of Embryos in Hogan et al., Manipulating the Mouse Embryos, A Laboratory Manual, $2^{nd}$ Ed. page 170-181. The embryos may be allowed to develop in utero or, alternatively, the fetus may be removed from the uterine environment before parturition.

d. Selecting a New Founder Pair from the Live Animals Produced

From the live animals produced in step (c), a brother-sister pair is selected to be a new founder pair to re-establish the foundation colony. All subsequent animals in the mouse strain will be derived from this new founder pair, until the process of using cryopreserved stock to re-establish the foundation colony is repeated, as described in the next section. Alternatively, a parent-offspring pair (e.g., father-daughter pair or mother-son pair can be selected to be a new founder pair. The following discussion refers to brother-sister pairs, but the parent-offspring can be used in place of brother-sister pairs.

A brother-sister pair may be selected randomly as a founder pair. Alternatively, the founder pair may be selected by phenotypic screening, genotypic screening, or a combination of both. Phenotypic screening may be conducted by visual inspection of, for example, coat color and behavior changes. Phenotypic screening may also be conducted by quantitative analysis of muscle grip strength, unrestrained measurements of respiratory rate, tidal volume and other respiratory indices with or without respiratory challenge, simultaneous measurements of $CO_2$ production, $O_2$ uptake, food and water intake, locomotor activity and circadian patterns, clinical chemistry test and blood chemistry test, expression profiling of sampled tissues. Genotypic screening may be conducted by examining a variety of indices, including, for example, biochemical and immunological markers isoenzymes, major histocompatibility complex (MHC), erythrocytic antigens, hemolytic complement (Hc—formerly C5), microsatellites and single nucleotide polymorphisms (SNPs). Genotypic screening can be carried out by any techniques available in the art, including, for example, PCR and sequencing. Proteomic screening can be carried out by any techniques available in the art, including for example, ELISA, mass spectrometry, flow cytometry, immunoassays and protein microarray.

e. Repeating Steps (c)-(d)

At an appropriate interval, the process of producing live animals from the pedigree-tracked stock and selecting a brother-sister as a new founder pair is repeated. An "appropriate interval" is an interval used to re-establish a foundation colony using the cryopreserved, frozen, freeze dried stock, that results in maintenance of genetic stability of an inbred strain. The appropriate interval can be empirically determined for a strain, such as by assessing the rate of genetic drift in the strain. The appropriate interval thus determined will vary among different inbred animal species and among different strains within the same animal species. Alternatively, an appropriate interval may be a pre-defined interval. An appropriate interval may be any number of generations between 1 and 40, such as, for example, every generation, every 5 generations, every 10 generations, every 15 generations, every 20 generations or every 40 generations.

Another aspect of the present invention relates to methods of maintaining genetic stability of an inbred animal strain. The methods include producing live animals from cryopreserved embryos of a pedigree-tracked stock derived from the foundation colony of the inbred strain, using a brother-sister pair selected from the live animals as a new founder pair and repeating the procedure at appropriate intervals.

Still another aspect of the present invention provides pedigree-tracked stocks of cryopreserved embryos derived from a foundation colony. The pedigree-stocks may be produced by any of the methods described herein or any variation of these methods. Such pedigree-tracked cryopreserved embryos may be used to re-establish the foundation colony at appropriate intervals. In one embodiment, the pedigree-tracked cryopreserved embryos include only embryos obtained by breeding a single brother-sister founder pair. In another embodiment, the pedigree-tracked cryopreserved embryos include embryos obtained by breeding more than one brother-sister pair derived from the foundation colony.

A further aspect of the present invention relates to genetically stabilized non-human animal inbred strains (e.g., inbred mouse strains, inbred mouse claims) made by the methods described herein.

A still further aspect of the present invention provides a business method of supplying non-human animal inbred strains with limited genetic drift. The method includes: (1) maintaining a foundation colony of the inbred strain; (2) producing a pedigree-tracked stock of cryopreserved embryos derived from the foundation colony; (3) at an appropriate time, selecting cryopreserved embryos that are siblings, and produce live animals from the embryos; (4) selecting a brother-sister pair from the animals produced and using them as a new founder pair to derive future animals in the strain; (5) repeating steps (1) to (4) at appropriate intervals and (6) providing animals to customer in response to a customer's order.

II. Maintaining Genetic Stability Using Cryopreserved Gametes or Pre-Gametes Stock As an alternative to using embryos, gametes or pre-gametes derived from a foundation colony of an inbred strain may be used to create a pedigree-tracked stock for the purpose of maintaining the genetic stability of an inbred strain.

Described herein are methods of maintaining genetic stability of an inbred strain, comprising: (1) maintaining a foundation colony of an inbred strain; (2) producing a pedigree-tracked stock of cryopreserved gametes or pre-gametes derived from the foundation colony; (3) at appropriate intervals, selecting cryopreserved gametes or pre-gametes that are obtained from a single brother-sister pair, and producing live animals from them; (4) selecting a brother-sister pair from the resulting animals and using them as a new founder pair to produce animals in the strain; and (5) repeating steps (3) to (4) at appropriate intervals.

Alternatively, the gametes or pre-gametes are freeze-dried. For example, freeze-dried sperm can be stored at room temperature, 4° C., −20° C., −80° C., −136° C., −196° C. (Kaneko et al. Comp Med. 2005 April; 55(2): 140-4; Y. Kawase, N. A. Wada, K. Jishage 2009, Theriogenology, in press; Elmoazzen et al. 2009, Cryobiology, Volume 59, Issue 1, pages 113-115.

The term "gamete" as used herein refers to any male or female germ cell that is capable of initiating formation of a new diploid individual. Examples of gametes are sperm and oocytes. Gametes can be present in fluids, tissues, and organs collected from animals (e.g., sperm is present seminal fluid; in semen, epididymis, oocytes in ovary).

The term "pre-gamete" includes any precursors that are capable of giving rise to gametes. Such precursors may be progenitor cells of the gametes. Progenitor cells for sperm include, but are not limited to, primordial germ cells, spermatogonia (including type A1, A2, A3 and A4 spermatogonia), spermatogonial stem cells, intermediate spermatogonium, type B spermatogonia, primary spermatocytes, secondary spermatocytes and spermatids. Progenitor cells for oocyte include, but not limited to, primordial germ cells, primordial follicles, oogonia, primary oocytes and secondary oocytes. Such precursors may also be embryonic stem cells, which are capable of giving rise to gametes. See, for example, Hubner et al., Science 300: 1251-6 (2003). The term "pre-gamete" also refers to any cell, tissue or organ capable of giving rise to gametes, such as, ovary and testes. In some instances, the tissue or organ capable of giving rise to gametes includes both gametes and pre-gametes. For example, ovaries contain gametes (oocytes) and pre-gametes (progenitor cells for oocytes).

A primordial germ cell is a diploid somatic cell capable of becoming a germ cell. Primordial germ cells can be isolated, for example, from the genital ridge. The genital ridge is a known defined region of the developing embryo, and is well-known to a person of ordinary skill in the art. See, e.g., Strelchenko, 1996, Theriogenology 45: 130-141 and Lavoir 1994, J. Reprod. Dev. 37: 413-424.

One aspect of the present invention relates to methods of producing a pedigree-tracked stock of cryopreserved, freeze-dried, frozen or other appropriately preserved gametes or pre-gametes derived from a foundation colony.

The number of gametes or pre-gametes necessary to create a pedigree-tracked stock for maintaining genetic stability is determined using the same set of considerations for embryo stocks. Likewise, the number of animals needed to produce sufficient number of gametes or pre-gametes for the stock is determined with the same considerations as in the context of embryo stocks, as discussed above. Thus, gametes or pre-gametes may be obtained from a founder pair directly. Alternatively, as for embryo stocks, the foundation colony is first expanded to produce sufficient numbers of brother-sister pairs and gametes and pre-gametes may then be obtained from these brother-sister pairs.

Gametes and pre-gametes are obtained from brother-sister pairs that are either live animals or embryos. Techniques for obtaining gametes or pre-gametes are known in the art. See, for example, Ogura and Yanagimachi, 1995, and Kubota et al., 2003.

Gametes and pre-gametes may be cryopreserved or freeze dried using any method known in the art. See, for example, U.S. Pat. No. 5,758,763, entitled "Methods for Cryopreservation of Primordial Germ Cells and Germ Cells", U.S. Application No. 20020131957, entitled "Cryopreservation of Sperm", Sztein et al., Biol. Reprod. 58: 1071-1074 (1998) and Candy et al, 2000.

Pedigree-tracked gametes or a pre-gamete stock is a stock in which the pedigree of each gamete or pre-gamete within the stock is known. Pedigrees of the gametes or pre-gametes may be tracked by following their pedigree and recording the pedigree information. For example, each gamete or pre-gamete may be separately labeled with its pedigree information. For another example, gametes or pre-gametes from single individuals may be physically stored and labeled as a sibling group. In this manner, one is able to select only gametes or pre-gametes that are obtained from a single brother-sister future pair. For example, gametes may be stored in a manner enabling one to select only eggs from a particular female and sperm from the female's brother.

At appropriate intervals, one may select cryopreserved or freeze-dried gametes or pre-gametes that are obtained from a single brother-sister pair, and produce live animals from them. Cryopreserved or freeze dried pre-gametes may be thawed or reconstituted and cultured under suitable conditions for the pre-gametes to give rise to gametes, which are then undergo in vitro fertilization to produce live animals.

In one embodiment, oocytes are collected from superovulated females and cryopreserved. Sperm are collected from respective male siblings and cryopreserved. At appropriate intervals, oocytes and sperm from siblings are thawed or reconstituted and used to produce embryos by IVF. Resulting embryos are transferred to pseudopregnant recipients to generate offspring.

In another embodiment, ovaries are collected from superovulated females and cryopreserved. Sperm are collected from respective male siblings or male parent and cryopreserved. At appropriate intervals, ovaries and sperm from siblings are thawed and used to produce embryos by IVF or AI. Resulting embryos are transferred to at least one (one or more) pseudopregnant recipient(s) to generate offspring. The recipients are maintained under conditions suitable for/that result in development of offspring.

Another embodiment described herein is methods of maintaining genetic stability of an inbred animal strain. The methods include producing live animals from cryopreserved gametes or pre-gametes of a pedigree-tracked stock derived from the foundation colony of the inbred strain, using a brother-sister or parent-child pair selected from the live animals as a new founder pair and repeating the procedure at appropriate intervals.

Still another embodiment is pedigree-tracked stocks of cryopreserved, gametes or pre-gametes derived from a foundation colony. Such pedigree-tracked stock may be used to re-establish the foundation colony at appropriate intervals.

Some aspects of the present invention provide pedigree-tracked stocks of freeze-dried gametes or pre-gametes derived from a foundation colony. Such pedigree-tracked stock may be used to re-establish the foundation colony at appropriate intervals.

A further aspect of the present invention relates to a genetically stabilized non-human animal inbred strain made by the methods described herein.

A still further aspect of the present invention provides a business method of supplying non-human animal inbred strains with limited genetic drift. The method includes: (1) maintaining a foundation colony of an inbred strain; (2) producing a pedigree-tracked stock of cryopreserved or freeze-dried gametes or pre-gametes derived from the foundation colony; (3) at appropriate intervals, selecting cryopreserved or freeze-dried gametes or pre-gametes that are obtained from a single brother-sister pair, and producing live animals from them; (4) selecting a brother-sister pair from the resulting animals and using them as a new founder pair to produce future animals in the strain; (5) repeating steps (3) to (4). The method can optionally comprise a further step (e.g., step 6) of providing a mouse to a customer in response to the customer's order.

III. Maintaining Genetic Stability Using One Founder Male

In this embodiment, at least one (a, one or more) inbred founder pair (brother-sister, or a parent-offspring pair) is selected. In one specific embodiment, the selected founder male is mated at least once with the founder female (sister or daughter) and, subsequently, the founder male is anesthetized to remove one epididymis/vas deferens and isolate the sperm which is collected, pedigree-tracked and cryopreserved or freeze-dried in aliquots in, for example, but not limited to, 10, 50, 100, 200, 300, 400, 500 or 1000 straws or other suitable containers, to establish foundation sperm stock. Foundation sperm stock is pedigree-tracked sperm obtained from the male of an inbred founder pair. In some embodiments, the foundation sperm stock is cryopreserved, freeze dried or frozen. After recovery from surgery, the founder male is used for further breeding with the founder female (sister or daughter) to produce offspring. The female offspring (F1) of this mating are used for breeding, such as by mating, with the founder male or foundation sperm stock to either produce offspring (F2) for further breeding, such as by mating, with the foundation sperm stock, to produce another generation of offspring (F3), or to produce embryos that are cryopreserved and pedigree-tracked to establish cryopreserved embryo stock.

Alternatively, daughters from brother-sister-breeding or father-daughter-breeding are bred with sperm from the foundation sperm stock, such as by artificial insemination techniques, in vitro fertilization or ICSI to produce embryos that are pedigree-tracked and cryopreserved to establish the pedigree-tracked cryopreserved embryo stock.

In an alternative embodiment, the founder male is euthanized before or after one or more successful mating. Both epididymides and vas deferentia are removed and sperm is isolated and cryopreserved in aliquots (e.g., in any number of straws from, 1 to 1000 straws, such as 10, 50, 100, 200, 300, 400, 500 or 1000) and pedigree-tracked to produce the pedigree-tracked cryopreserved gamete stock, also called foundation sperm stock. The cryopreserved or freeze-dried foundation sperm stock is used for breeding with the founder female (sister or daughter) to produce offspring. The female offspring (F1) are used for breeding with the foundation sperm stock to produce more offspring which is carried out, until sufficient female offspring (F2, F3, F4, F5, . . . F20) are obtained. The resulting female offspring are used for breeding with foundation sperm stock to establish the pedigree-tracked, cryopreserved embryo stock. Alternatively, the female offspring (F1) of the founder pair breeding are used for breeding with foundation sperm stock to establish directly the pedigree-tracked, cryopreserved embryo stock.

In an alternative embodiment, sperm of the founder male is divided into fresh and cryopreserved or freeze-dried aliquots. The cryopreserved or freeze-dried founder male sperm is used to establish the pedigree-tracked, foundation sperm stock. The fresh founder male sperm is used for initial breeding with the founder female. All subsequent breeding will be done with the foundation sperm stock.

IV. Maintaining Genetic Stability Using Serial Ovary Transplantation to Generate a Cryopreserved Embryo Stock Another embodiment is a method of maintaining genetic stability of an inbred rodent (mouse, rat) strain, comprising (a) maintaining a pedigree-tracked stock of cryopreserved or freeze-dried rodent male gametes or a pedigree-tracked stock of cryopreserved or freeze-dried rodent male pre-gametes, wherein the cryopreserved or freeze-dried rodent male gametes or pre-gametes are obtained from at least one male of a pedigreed inbred breeding pair, wherein the inbred breeding pair comprises a brother-sister or parent-offspring pair; (b) selecting the rodent female from at least one pedigreed inbred breeding pair, wherein the inbred breeding pair comprises a brother-sister or parent-offspring pair and isolating both ovaries of this female, thereby producing pedigree-tracked ovaries; (c) dissecting each pedigree-tracked ovary into at least 2 fragments (e.g., into any number of fragments between 2 and 32, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 fragments) thereby producing at least two (two or more) pedigree-tracked ovary fragments or sections; (d) transplanting one or more of the pedigree tracked ovary fragments into one or more compatible host rodent female recipients, thereby producing at least one ovary transplanted rodent host female recipient (rodent host female into which at least one ovary fragment was transplanted); (e) isolating oocytes and ovary fragments from at least one of the transplanted host females produced in step (d); (f) transplanting ovary fragments obtained in step (e) into a new rodent host female recipient and repeating steps (d) and (e), in order to increase the oocyte potential of each ovary fragment and to shorten the breeding cycle; (g) breeding oocytes obtained in step (e) with rodent male gametes or pre-gametes of step (a), thereby producing embryos; (h) cryopreserving the embryos to establish the pedigree-tracked cryopreserved embryo stock; (i) producing live offspring from cryopreserved embryos produced in step (h); (j) selecting at least one pedigree-tracked inbred breeding pair from the live rodents obtained in step (i) to be used as a new founder pair to re-establish the foundation colony, wherein the inbred breeding pair is a brother-sister pair or a parent-offspring pair from which all subsequent rodents of the strain are derived; (k) breeding the new founder pair from step (j) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (l) replenishing the foundation colony by repeating steps (i) to (j) at intervals of 1 to 20 generations and, thus, inhibiting the accumulation of genotypic changes, thereby maintaining genetic stability of the inbred rodent strain.

Alternatively, the ovary transplanted rodent host female recipient is bred (mated) with rodent male gametes or pre-gametes to produce embryos. The ovary fragments of step (d) are isolated from the ovary transplanted host female recipient and further transplanted into another host female recipient (thereby producing a further ovary transplanted host female recipient). These steps are repeated in order to increase the oocyte potential of each ovary fragment.

In one embodiment the gametes or pre-gametes of the selected founder male of step (a) are isolated, pedigree-tracked and cryopreserved or freeze-dried in aliquots in, for example, but not limited to, 10, 50, 100, 200, 300, 400, 500 or more straws or other suitable containers, to establish the foundation stock of male gametes or pre-gametes (referred to as pedigree-tracked cryopreserved male gamete stock or male gamete stock).

In one embodiment the host female is ovariectomized In another embodiment the host female is sterile.

In one embodiment the host female is immunodeficient and ovariectomized In another embodiment the host female is immunodeficient and sterile. In one embodiment the host female is histocompatible to the ovary donor rodent (mouse/rat).

In one embodiment the host females are superovulated before the oocytes are isolated.

In one embodiment the ovary fragments are cryopreserved before transplantation. In another embodiment the ovary or ovary fragments are cryopreserved upon removal from the host female and thawed before transplantation into a new host female. In another embodiment whole ovaries are transplanted.

In one embodiment breeding is performed by IVF.

In one embodiment breeding is performed by AI.

In another embodiment breeding is performed by assisted IVF (for example zona drilling or zona cutting) or ICSI or surgical assisted artificial insemination.

In one embodiment embryos and ovary fragments are isolated after AI.

Another embodiment is a method of maintaining genetic stability of an inbred rodent (mouse, rat) strain, comprising (a) maintaining a pedigree-tracked stock of cryopreserved or freeze-dried rodent male gametes or a pedigree-tracked stock of cryopreserved or freeze-dried rodent male pre-gametes, wherein the cryopreserved or freeze-dried rodent male gametes or pre-gametes are obtained from at least one male of a pedigreed inbred breeding pair, wherein the inbred breeding pair comprises a brother-sister or parent-offspring pair; (b) selecting the rodent female from at least one pedigreed inbred breeding pair, wherein the inbred breeding pair comprises a brother-sister or parent-offspring pair and isolating both ovaries of this female, thereby producing pedigree-tracked ovaries; (c) dissecting each pedigree-tracked ovary into at least 2 fragments (e.g., into any number of fragments between 2 and 32, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 fragments) thereby producing at least two (two or more) pedigree-tracked ovary fragments or sections; (d) transplanting one or more of the pedigree tracked ovary fragments into one or more compatible host rodent female recipients, thereby producing at least one ovary transplanted rodent host female recipient (rodent host female into which at least one ovary fragment was transplanted); (e) breeding the rodent host female of step (d) with rodent male gametes or pre-gametes of step (a), thereby producing embryos; (f) isolating ovary fragments and embryos from host females of step (e); (g) cryopreserving the embryos to establish the pedigree-tracked cryopreserved embryo stock; (h) transplanting ovary fragments obtained in step (f) into a new rodent host female recipient and repeating steps (e) to (h) in order to increase the oocyte potential of each ovary fragment and to shorten the breeding cycle;

(i) producing live offspring from cryopreserved embryos produced in step (g); (j) selecting at least one pedigree-tracked inbred breeding pair from the live rodents obtained in step (i) to be used as a new founder pair to re-establish the foundation colony, wherein the inbred breeding pair is a brother-sister pair or a parent-offspring pair from which all subsequent rodents of the strain are derived; (k) breeding the new founder pair from step (j) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (l) replenishing the foundation colony by repeating steps (i) to (j) at intervals of 1 to 20 generations and, thus, inhibiting the accumulation of genotypic changes, thereby maintaining genetic stability of the inbred rodent strain.

In one embodiment the gametes or pre-gametes of the selected founder male are isolated, pedigree-tracked and cryopreserved or freeze-dried in aliquots in, for example, but not limited to, 10, 50, 100, 200, 300, 400, 500 or more straws or other suitable containers, to establish the foundation stock of male gametes or pre-gametes (referred to as pedigree-tracked cryopreserved male gamete stock or male gamete stock).

In one embodiment the host female is ovariectomized In another embodiment the host female is sterile.

In one embodiment the host female is immunodeficient and ovariectomized In another embodiment the host female is immunodeficient and sterile. In one embodiment the host female is histocompatible to the ovary donor rodent (mouse or rat).

In one embodiment the host females are superovulated before the oocytes are isolated.

In one embodiment the ovary fragments are cryopreserved before transplantation. In another embodiment the ovary or ovary fragments are cryopreserved upon removal from the host female and thawed before transplantation into a new host female. In another embodiment whole ovaries are transplanted.

In one embodiment breeding is performed by AI.

V. Maintaining Genetic Stability Using Serial Ovary Transplantation (Pre-Gamete Stock)

Another embodiment is a method of maintaining genetic stability of an inbred rodent (mouse, rat) strain, comprising (a) maintaining a pedigree-tracked stock of cryopreserved or freeze-dried rodent male gametes or a pedigree-tracked stock of cryopreserved or freeze-dried rodent male pre-gametes, wherein the cryopreserved or freeze-dried rodent male gametes or pre-gametes are obtained from at least one male of a pedigreed inbred breeding pair, wherein the inbred breeding pair comprises a brother-sister or parent-offspring pair; (b) selecting the rodent female from at least one pedigreed inbred breeding pair, wherein the inbred breeding pair comprises a brother-sister or parent-offspring pair and isolating both ovaries of this female, thereby producing pedigree-tracked ovaries; (c) dissecting each pedigree-tracked ovary into at least 2 fragments (e.g., into any number of fragments between 2 and 32, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 fragments) thereby producing at least two (two or more) pedigree-tracked ovary fragments or sections and cryopreserving or freeze-drying the pedigree-tracked ovary fragments or sections to establish a pedigree-tracked cryopreserved pre-gamete stock ; (d) transplanting one or more of the pedigree tracked ovary fragments into one or more compatible host rodent female recipients, thereby producing at least one ovary transplanted rodent host female recipient (rodent host female into which at least one ovary fragment was transplanted); (e) isolating oocytes and ovary fragments from at least one of the transplanted host females produced in step (d); (f) transplanting ovary fragments obtained in step (e) into a new rodent host female recipient and repeating steps (d) and (e), in order to increase the oocyte potential of each ovary fragment and to shorten the breeding cycle; (g) breeding oocytes obtained in step (e) with rodent male gametes or pre-gametes of step (a), (h) producing live offspring from breeding in step (g); (i) selecting at least one pedigree-tracked inbred breeding pair from the live rodents obtained in step (h) to be used as a new founder pair to re-establish the foundation colony, wherein the inbred breeding pair is a brother-sister pair or a parent-offspring pair from which all subsequent rodents of the strain are derived; (j) breeding the new founder pair from step (i) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (k) replenishing the foundation colony by repeating steps (g) to (j) at intervals of 1 to 20 generations and, thus, inhibiting the accumulation of genotypic changes, thereby maintaining genetic stability of the inbred rodent strain.

Alternatively, the ovary transplanted rodent host female recipient is bred (mated) with rodent male gametes or pre-gametes to produce embryos. The ovary fragments of step (d) are isolated from the ovary transplanted host female recipient and further transplanted into another host female recipient (thereby producing a further ovary transplanted host female recipient). These steps are repeated in order to increase the oocyte potential of each ovary fragment.

In one embodiment the gametes or pre-gametes of the selected founder male are isolated, pedigree-tracked obtained in step (a) are cryopreserved or freeze-dried in aliquots in, for example, but not limited to, 10, 50, 100, 200, 300, 400, 500 or more straws or other suitable containers, to establish the foundation stock of male gametes or pre-gametes (referred to as pedigree-tracked cryopreserved male gamete stock or male gamete stock).

In one embodiment the host female is ovariectomized In another embodiment the host female is sterile.

In one embodiment the host female is immunodeficient and ovariectomized In another embodiment the host female is immunodeficient and sterile. In one embodiment the host female is histocompatible to the ovary donor rodent (mouse/rat).

In one embodiment the host females are superovulated before the oocytes are isolated. In one embodiment the ovary fragments are cryopreserved before transplantation.

In another embodiment the ovary or ovary fragments are cryopreserved upon removal from the host female and thawed before transplantation into a new host female.

In another embodiment whole ovaries are transplanted.

In one embodiment breeding is performed by IVF. In another embodiment breeding is performed by AI. In another embodiment breeding is performed by assisted IVF (for example zona drilling or zona cutting) or ICSI or surgical assisted artificial insemination.

Embodiments of Methods of Maintaining Genetic Stability Using Pedigree-Tracked Cryopreserved or Freeze Dried Gametes or Pre-Gametes Stock Embodiments 1 One embodiment is a method of maintaining genetic stability of an inbred rodent strain, comprising: (a) establishing a foundation colony of an inbred rodent strain, wherein the foundation colony comprises only brother-sister pairs, parent-offspring pairs or brother-sister pairs and parent-offspring pairs from which all subsequent rodents of the strain are derived; (b) selecting at least one (one or more, a) pedigreed inbred breeding pair as a founder pair from the foundation colony, wherein the founder pair is a brother-sister pair or a parent-offspring pair from which all subsequent rodents of the strain are derived; (c) breeding the founder pair selected in step (b) to produce at least one (one or more, a) female offspring; (d) maintaining a stock of cryopreserved or freeze dried pre-gametes and/or gametes obtained from the male of the founder pair of step (b); (e) obtaining rodent embryos by breeding the at least one female offspring obtained in step (c) with the male of the founder pair of step (b) and cryopreserving the rodent embryos; (f) producing at least one live female rodent from cryopreserved rodent embryos obtained in step (e); (g) re-establishing the foundation colony by breeding the at least one female live rodent obtained in step (f) using the stock of cryopreserved pre-gametes and/or gametes obtained in step (d) to produce offspring; (h) replenishing the foundation colony by repeating steps (f) to (g) at intervals of 1 to 20 generations and thus, inhibiting the accumulation of genotypic or genetic changes, thereby maintaining genetic stability of the inbred rodent strain.

In this embodiment and others described herein, methods described herein and methods known to those of skill in the art can be used to breed animals, obtain resulting rodent embryos, optionally, as needed, cryopreserve them and subsequently prepare them to produce offspring.

Embodiment 2 Another embodiment is a method of maintaining genetic stability of an inbred rodent strain, comprising: (a) establishing a foundation colony of an inbred rodent strain, wherein the foundation colony comprises only brother-sister pairs, parent-offspring pairs or brother-sister pairs and parent-offspring pairs from which all subsequent rodents of the strain are derived; (b) selecting at least one (one or more, a) pedigreed inbred breeding pair as a founder pair from the foundation colony, wherein the founder pair is a brother-sister pair or a parent-offspring pair from which all subsequent rodents of the strain are derived; (c) breeding the founder pair selected in step (b) to produce at least one (one or more, a) female offspring; (d) maintaining a stock of cryopreserved or freeze dried pre-gametes and/or gametes obtained from the male of the founder pair of step (b); (e) obtaining rodent embryos by breeding the at least one female offspring obtained in step (c) with the male of the founder pair of step (b) and cryopreserving the rodent embryos; (f) producing live rodents from cryopreserved rodent embryos obtained in step (e); (g) re-establishing the foundation colony by selecting a pedigreed inbred breeding pair from the live rodents obtained in step (f) and breeding them to produce offspring, wherein the inbred breeding pair is a brother-sister or a parent-offspring pair from which all subsequent rodents of the strain are derived; (h) replenishing the foundation colony by repeating steps (f) to (g) at intervals of 1 to 20 generations and thus, inhibiting the accumulation of genotypic changes, thereby maintaining genetic stability of the inbred rodent strain.

In another embodiment the gametes or pre-gametes of the male founder are cryopreserved or freeze-dried before breeding (and a pedigreed stock is prepared).

Embodiments 3+4 In either of the embodiments described above, the cryopreserved or freeze dried pre-gametes and/or gametes in step (d) comprise cryopreserved or freeze dried sperm, cryopreserved or freeze dried spermatids, cryopreserved or freeze dried spermatocyte, cryopreserved or freeze dried spermatogonia, cryopreserved or freeze dried spermatogonial stem cells or germ cells. In addition, the cryopreserved or freeze dried pre-gametes in step (d) can be (are) matured in vitro or in vivo to gametes.

Embodiment 5 A further embodiment is a method of maintaining genetic stability of an inbred rodent strain, comprising: (a) breeding a founder pair to produce at least one (one or more, a) female offspring and at least one (one or more, a) male offspring, wherein the founder pair is a brother-sister pair or a parent-offspring pair; (b) maintaining a pedigree-tracked stock of cryopreserved or freeze dried rodent pre-gametes and/or gametes, wherein the pre-gametes and/or gametes are obtained from the at least one female offspring and the at least one male offspring of step (a); (c) breeding the female pre-gametes or gametes obtained in step (b) with the pedigree-tracked cryopreserved or freeze dried male pre-gametes or gametes of step (b) to produce live rodents; (d) selecting at least one pedigreed inbred breeding pair from the live rodents obtained in step (c) to be used as a new founder pair to re-establish the foundation colony, wherein the inbred breeding pair is a brother-sister pair, parent-offspring pair from which all subsequent rodents of the strain are derived; (e) breeding the new founder pair from step (d) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (f) replenishing the foundation colony by repeating steps (c) to (e) at intervals of 1 to 20 generations and thus, inhibiting the accumulation of genotypic changes, thereby maintaining genetic stability of the inbred rodent strain. In one embodiment, the female gametes are isolated from ovaries.

In another embodiment the ovaries are divided into fragments. In another embodiment the female pre-gametes are follicles, immature oocytes or germ cells which are matured in vitro before breeding. In another embodiment the female pre-gametes are follicles which are matured in vivo before breeding. In another embodiment the ovaries or ovary fragments are implanted into a host nonhuman (e.g., rodent) female before breeding. In one embodiment the female is superovulated before gametes or pre-gametes are collected. In another embodiment the host nonhuman female (e.g., host rodent female) is superovulated after ovary transplantation and before breeding. In one embodiment, the male gametes are sperm. In one embodiment, the male pre-gametes are spermatids. In another embodiment the male pre-gametes are spermatids, spermatogonial stem cells or germ cells, which are matured in vitro before breeding. In another embodiment the male pre-gametes are spermatogonial stem cells which are matured in vivo before breeding. In one embodiment breeding is done by artificial insemination, surgical assisted artificial insemination, in vitro fertilization, IVF combined with zona drilling or zona cutting, or intracytoplasmic sperm or haploid spermatid injection (ICSI), or electrofusion.

Embodiment 6 An additional embodiment is a method of maintaining genetic stability of an inbred rodent strain, comprising: (a) breeding a founder pair to produce at least one female offspring and at least one male offspring, wherein the founder pair is a brother-sister pair or a parent-offspring pair: (b) isolating a pedigree-tracked stock of rodent pre-gametes and/or gametes, wherein the rodent pre-gametes and/or gametes are obtained from the at least one female offspring and the at least one male offspring of step (a); (c) breeding the pedigree-tracked stock of rodent pre-gametes and/or gametes of step (b) to produce rodent embryos, and cryopreserving the rodent embryos; (d) producing live rodents from cryopreserved rodent embryos obtained in step (c); (e) selecting at least one pedigreed inbred breeding pair from the live rodents obtained in step (d) to be used as a new founder pair to re-establish the foundation colony, wherein the inbred breeding pair is a brother-sister pair, parent-offspring pair from which all subsequent rodents of the strain are derived; (f) breeding the new founder pair from step (e) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (g) replenishing the foundation colony by repeating steps (d) to (f) at intervals of 1 to 20 generations and thus, inhibiting the accumulation of genotypic changes, thereby maintaining genetic stability of the inbred rodent strain.

Embodiment 7 A further embodiment is a method of maintaining genetic stability of an inbred rodent strain, comprising: (a) isolating a pedigree-tracked stock of rodent gametes or a pedigree-tracked stock of rodent pre-gametes from at least one pedigreed inbred breeding pair, wherein the inbred breeding pair comprises a brother sister pair or a parent-offspring pair; (b) producing rodent embryos from the pedigree-tracked stock of rodent gametes or rodent pre-gametes obtained in step (a) by breeding with the pedigree-tracked of female and male gametes or pre-gametes of step (a) and cryopreserving rodent embryos; (c) producing live rodents from cryopreserved rodent embryos obtained in step (b); (d) selecting at least one pedigreed inbred breeding pair from the live rodents obtained in step (c) to be used as a new founder pair to re-establish the foundation colony, wherein the inbred breeding pair is a brother-sister pair, parent-offspring pair from which all subsequent rodents of the strain are derived; (e) breeding the new founder pair from step (c) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (f) replenishing the foundation colony by repeating steps (c) to (e) at intervals of 1 to 20 generations and, thus, inhibiting the accumulation of genotypic changes, thereby maintaining genetic stability of the inbred rodent strain.

Embodiment 8 Another embodiment is a method of maintaining genetic stability of an inbred rodent strain, comprising: (a) maintaining a pedigree-tracked stock of cryopreserved rodent gametes or a pedigree-tracked stock of cryopreserved rodent pre-gametes, wherein the cryopreserved rodent gametes or pre-gametes are obtained from at least one pedigreed inbred breeding pair, wherein the inbred breeding pair comprises a brother-sister pair or a parent-offspring pair; (b) breeding the female gametes or pre-gametes of step (a) with the pedigree-tracked stock of male gametes or pre-gametes of step (a) to produce live rodents; (c) selecting at least one pedigreed inbred breeding pair from the live rodents obtained in step (b) to be used as a new founder pair to re-establish the foundation colony, wherein the inbred breeding pair is a brother-sister pair, parent-offspring pair from which all subsequent rodents of the strain are derived; (d) breeding the new founder pair from step (c) to produce offspring and thereby re-establish the foundation colony, wherein the foundation colony is a colony of only brother-sister pairs; parent-offspring pairs; or brother-sister pairs and parent-offspring pairs from which all subsequent rodents of the strain are derived; and (e) replenishing the foundation colony by repeating steps (b) to (d) at intervals of 1 to 20 generations and thus, inhibiting the accumulation of genotypic changes, thereby maintaining genetic stability of the inbred rodent strain.

Embodiment 9 A further embodiment is a method of maintaining genetic stability of an inbred rodent strain, comprising: (a) establishing a foundation colony of an inbred rodent strain, wherein the foundation colony comprises only brother-sister pairs, parent-offspring pairs or brother-sister pairs and parent-offspring pairs from which all subsequent rodents of the strain are derived; (b) selecting at least one pedigreed inbred breeding pair as a founder pair from the foundation colony, wherein the founder pair is a brother-sister pair or a parent-offspring pair from which all subsequent rodents of the strain are derived; (c) isolating the pre-gametes from the founder female selected in step (b); (d) obtaining rodent embryos by breeding the pre-gametes of host females obtained in step (c) with the founder male selected in step (b) and cryopreserving the rodent embryos; (e) producing live rodents from cryopreserved rodent embryos obtained in step (d); (f) re-establishing the foundation colony by selecting a pedigreed inbred breeding pair from the live rodents obtained in step (e) and breeding them to produce offspring, wherein the inbred breeding pair is a brother-sister pair from which all subsequent rodents of the inbred strain are derived; (h) replenishing the foundation colony by repeating steps (e) to (f) at intervals of 1 to 20 generations and thus, inhibiting the accumulation of genotypic changes, thereby maintaining genetic stability of the inbred rodent strain.

Embodiments 10-13 In any of the embodiments in which female gametes are used, they can comprise oocytes or ovary. In any of the embodiments in which female pre-gametes are used, they can comprise ovary, germ cells, oogonia, primary oocytes or secondary oocytes. In any of the embodiments in which male gametes are used, they can comprise sperm. In any of the embodiments in which male pre-gametes are used, they can comprise spermatogonial stem cell, spermatogonia, spermatid, haploid, spermatids, primary spermatocyte or germ cells.

Embodiment 14 In embodiments 5, 6, 7, 8, and 9, the pre-gametes can be matured in vitro or in vivo into gametes.

Embodiment 15 In embodiments 6, 7, and 9, the pre-gametes or gametes can be fresh or cryopreserved or freeze-dried.

Embodiment 16 In embodiments 5, 6, 7, 8 and 9, the female pre-gametes can be transplanted into at least one new host recipient before breeding.

Embodiment 17 In embodiments 5, 6, 7 and 8, the male pre-gametes can be transplanted into at least one new host recipient before breeding.

Embodiment 18 In embodiments 5, 6, 7 and 8, the pedigreed inbred breeding pair of step (a) is one single inbred breeding pair.

Embodiment 19 In embodiment 9, the pedigreed inbred breeding pair of step (b) can be one single inbred breeding pair.

In all embodiments, ovaries and ovary fragments and sperm can be frozen directly from the founder female or male without expansion or using serial transfer.

Embodiment 20 In embodiments 5, 6, 7, 8 and 9, the female pre-gametes are ovaries and the ovaries can be used intact (undivided) or are subdivided into at least 2 fragments per ovary.

Embodiment 21 In embodiments 5, 6,7 8, and 9, two ovary fragments are transplanted into one new host female recipient before breeding.

Embodiment 22 In embodiments 5, 6, 7, 8 and 9, the pedigree-tracked stock of rodent female pre-gametes comprises (i) isolating ovaries from the at least one pedigree-tracked founder female or founder female offspring; (ii) sub-dividing the ovaries into fragments, thereby producing ovary fragments; (iii) cryopreserving the ovary fragments of step (ii) in containers such that each container comprises ovary fragments from the same female.

Embodiment 23 In embodiments 5, 6, 7, 8 and 9, (i) the female pre-gametes are ovaries or ovary fragments that are transplanted into at least one female host recipient, followed by breeding the host female recipient(s) with pedigree-tracked male gamete(s) isolated from a male founder who is either brother or father to the female from whom the pre-gametes were obtained; (ii) ovaries or ovary fragments from the host female recipient(s) of step (i) are isolated and pedigree-tracked and transplanted into a different (subsequent) host female recipient, who is then bred with pedigree-tracked male gamete(s) isolated from the male founder; (iii) step (ii) is repeated at appropriate intervals, thereby extending the gamete potential of the ovary or ovary fragment.

Embodiment 24 In the above embodiment, the female pre-gametes are cryopreserved before breeding.

Embodiment 25 In embodiment 23, the male pre-gametes are cryopreserved or freeze-dried before breeding.

Embodiment 26 In embodiment 23, breeding is carried out by assisted reproductive techniques, such as in vitro fertilization, intracytoplasmic sperm injection or artificial insemination (AI). In some embodiments, breeding is carried out by surgical assisted artificial insemination.

Maturation of Pre-Gametes

Immature Oocytes

In one embodiment fully grown, meiotically competent oocytes are collected from the ovary, matured and fertilized in vitro, as described, for example, by Schroeder and Eppig, 1984. For example, females can be primed with PMSG (pregnant mare serum gonadotropin) and immature oocytes can be isolated and cryopreserved. Oocytes may also be fertilized using cryopreserved sperm using IVF or ICSI.

Primordial Follicles

The oocyte pool is established near the time of birth when oogonia enter meiosis, become oocytes and form primordial follicles. In one embodiment primordial follicles are collected, grown in vitro and used to produce offspring (Eppig and Schroeder, 1989; Aerts et al, 2009; Liu et al, 2000; Shikanov et al., 2009). Alternatively, follicle free systems may also be a feasible approach to producing large numbers of oocytes from a single female (Honda et al 2009).

Ovaries contain primordial follicles. The cryopreservation of the ovary is a method to cryopreserve primordial follicles. Ovaries function normally after thawing and transplantation. When ovaries are transplanted into a new host female, the primordial follicles will mature and produce oocytes.

Spermatids/Spermatocytes

Spermatids, also know as round spermatids, are haploid spermatogenic cells. In one embodiment spermatids are isolated from the testis and cryopreserved to produce a pre-gamete stock. The thawed spermatids can be used directly for oocyte fertilizing to produce embryos and live offspring. Fertilization may be achieved by electrofusion (Ogura A, Matsuda J, Yanagimachi R. Birth of normal young after electrofusion of mouse oocytes with round spermatids. Proc Natl Acad Sci USA 1994 91:7460-7462) or ICSI (Kimura Y, Yanagimachi R. Mouse oocytes injected with testicular spermatozoa or round spermatids can develop into normal offspring. Development 1995 121:2397-2405; Ogura et al. 1996, J Assist Reprod Genet. Vol. 13(5), p 431-434; Hirabayashi M, Kato M, Aoto T, Ueda M, Hochi S. Rescue of infertile transgenic rat lines by intracytoplasmic injection of cryopreserved round spermatids. Mol Reprod Dev 2002 62:295-299; Movahedin et al 2004, Andrologia. 2004 October; 36(5):269-76).

In another embodiment spermatids are differentiated in vitro from spermatocytes (Marh et al, 2003, Biology of Reproduction, vol. 69, p 169-176). Spermatocytes are isolated from testis and cultured in vitro, for example as a co-culture with Sertoli cells or other culture conditions known in the art (Movahedin et al 2004, Andrologia. 2004 October; 36(5):269-76). The resulting spermatids can be cryopreserved to produce a pre-gamete stock.

In another embodiment spermatocytes can be cryopreserved or freeze-dried to produce a pre-gamete stock.

Spermatogonial Stem Cells/Testis Transplantation

The testes maintain a self-renewing population of stem cells from which spermatozoa develop. These spermatogonial stem cells (SSCs) can be cryopreserved (Avarbock et al, 1996) and used as a source of gametes.

In one embodiment SSCs are injected into the seminiferous tubules of one or more suitable host mouse (Brinster and Avarbock, 1994). After repopulation of the testis, males can be mated, or sperm can be collected and used for AI, IVF, assisted IVF or ICSI.

Transplantation of Testis Cells

In one embodiment the testes from a founder male are isolated and a single cell suspension of the testis is prepared. The single cell suspension may be prepared by mechanical dissociation or by enzymatic digestion (for example using collagenase and trypsin or other suitable enzymes). The cell suspension can be cryopreserved and used to establish the pre-gamete stock.

After thawing, the cells can be transplanted into a suitable host mouse. For example the cells can be injected into the seminiferous tubules of the testes. $1 \times 10^3$ to $1 \times 10^6$ cells may be injected. The injection may be done once or several times, for example 1 week, 2, weeks, 3 weeks, 4 weeks after the initial injection.

After repopulation of the testis, males can be mated, or sperm can be collected and used for AI, IVF, assisted IVF or ICSI.

Transplantation of Testicular Pieces

In some embodiments, testicular pieces of a founder male are isolated and then either directly transplanted or cryopreserved and then transplanted.

Following transplantation, spermatogenesis resumes, and gametes or pre-gametes can be collected for use in AI, IVF, assisted IVF or ICSI (Shinohara et al, 2002, Hum Reprod. Vol. 17(12):3039-45).

Germ Cells

In one embodiment, germ cells of the male founder and the female founder are isolated and cryopreserved or freeze-dried to establish the pre-gamete stock. Germ cells can be differentiated in vitro into gametes (Chuma et al 2005; Shen et al 2006). The gametes obtained can be used for IVF, assisted IVF or ICSI.

REFERENCES

Yuan Z, Hou R, Wu J., Generation of mice by transplantation of an adult spermatogonial cell line after cryopreservation. Cell Prolif. 2009 April; 42(2):123-31.

Movahedin M, Ajeen A, Ghorbanzadeh N, Tiraihi T, Valojerdi M R, Kazemnejad A., In vitro maturation of fresh and frozen-thawed mouse round spermatids. Andrologia. 2004 October; 36(5):269-76.

Shinohara T, Inoue K, Ogonuki N, Kanatsu-Shinohara M, Miki H, Nakata K, Kurome M, Nagashima H, Toyokuni S, Kogishi K, Honjo T, Ogura A., Birth of offspring following transplantation of cryopreserved immature testicular pieces and in-vitro microinsemination. Hum Reprod. 2002; 17(12): 3039-45.

Ogura A, Matsuda J, Asano T, Suzuki O, Yanagimachi R., Mouse oocytes injected with cryopreserved round spermatids can develop into normal offspring. J Assist Reprod Genet. 1996 May; 13(5):431-4.

Schroeder A C, Eppig J J., The developmental capacity of mouse oocytes that matured spontaneously in vitro is normal. Dev Biol. 1984 April; 102(2):493-7.

Eroglu A, Toner M, Leykin L, Toth T L., Cytoskeleton and polyploidy after maturation and fertilization of cryopreserved germinal vesicle-stage mouse oocytes. J Assist Reprod Genet. 1998 August; 15(7):447-54.

Eppig J J, Schroeder A C., Capacity of mouse oocytes from preantral follicles to undergo embryogenesis and development to live young after growth, maturation, and fertilization in vitro. Biol Reprod. 1989 August; 41(2):268-76.

Aerts J M, Martinez-Madrid B, Leroy J L, Van Aelst S, Bols P E., Xenotransplantation by injection of a suspension of isolated preantral ovarian follicles and stroma cells under the kidney capsule of nude mice. Fertil Steril. 2009 May 5. [Epub ahead of print]

Shikanov A, Xu M, Woodruff T K, Shea L D., Interpenetrating fibrin-alginate matrices for in vitro ovarian follicle development. Biomaterials. 2009 October; 30(29):5476-85. Epub 2009 Jul. 18.

Liu J, Van Der Elst J, Van Den Broecke R, Dumortier F, Dhont M., Maturation of mouse primordial follicles by combination of grafting and in vitro culture. Biol Reprod. 2000 May; 62(5):1218-23.

Chuma S, Kanatsu-Shinohara M, Inoue K, Ogonuki N, Mild H, Toyokuni S, Hosokawa M, Nakatsuji N, Ogura A, Shinohara T., Spermatogenesis from epiblast and primordial germ cells following transplantation into postnatal mouse testis. Development. 2005 January; 132(1):117-22. Epub 2004 Dec. 2.

Honda A, Hirose M, Inoue K, Hiura H, Mild H, Ogonuki N, Sugimoto M, Abe K, Kanatsu-Shinohara M, Kono T, Shinohara T, Ogura A., Large-scale production of growing oocytes in vitro from neonatal mouse ovaries. Int J Dev Biol. 2009; 53(4):605-13.

Avarbock M R, Brinster C J, Brinster R L., Reconstitution of spermatogenesis from frozen spermatogonial stem cells. Nat Med. 1996 June; 2(6):693-6.

Brinster R L, Avarbock M R., Germline transmission of donor haplotype following spermatogonial transplantation. Proc Natl Acad Sci USA. 1994, 91(24):11303-7.

Feng L X, Chen Y, Dettin L, Pera R A, Herr J C, Goldberg E, Dym M., Generation and in vitro differentiation of a spermatogonial cell line. Science. 2002; 297(5580):392-5.

Shen W, Zhang D, Qing T, Cheng J, Bai Z, Shi Y, Ding M, Deng H., Live offspring produced by mouse oocytes derived from premeiotic fetal germ cells. Biol Reprod. 2006, 75(4): 615-23.

III. Maintaining Genetic Stability Using Cryopreserved ES Cell Stock

As an alternative to using embryos gametes or pre-gametes, embryonic stem cells derived from a foundation colony of an inbred strain may be used to create a pedigree-tracked stock for the purpose of maintaining the genetic stability of an inbred strain.

Accordingly, the present invention provides methods of maintaining genetic stability of an inbred strain, comprising: (1) maintaining a foundation colony of an inbred strain; (2) producing a pedigree-tracked stock of cryopreserved embryos derived from the foundation colony; (3) at appropriate intervals, selecting cryopreserved embryonic stem cells that are obtained from a single brother-sister pair, and producing live animals from them; (4) selecting a brother-sister pair from the animals produced and using them as a new founder pair to derive future animals in the strain; and (5) repeating steps (3) to (4) at appropriate intervals.

An embryonic stem cell (ES cell) is a pluripotent cell isolated from an embryo. ES cells may be cultured in vitro with or without feeder cells. ES cells can be established from embryonic cells isolated from early embryos, principally from blastocyst stage embryos. The methods for both ES cell establishment and culture are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, Theriogenology 38: 315-335, both of which are incorporated herein by reference in their entireties. The term "embryonic stem cell" or "ES cell" as used herein, includes ES cell lines.

ES cells of the pedigree-tracked stock can be obtained from embryos produced by breeding a brother-sister pair of the foundation colony. Such techniques are well-known to those skilled in the art. The ES cells are then cryopreserved and stored in a manner to allow one to select only ES cells obtained from a single brother-sister pair. Preferably, the ES cells are cryopreserved at an early passage, such as, for example, within 3-20 passages.

The number of frozen units of ES cells necessary to create a pedigree-tracked stock for maintaining genetic stability depends on many factors, including, for example, the length of time over which a genetic stability is to be maintained, the frequency with which the cryopreserved stock is used to re-establish a foundation colony, the efficiency of producing live animals from cryopreserved ES cells and the efficiency of the ES cells to give rise to live animals that are derived completely from the ES cells. These factors will differ not only among different animal species, but among different strains of the same animal species.

ES cells may be obtained from embryos resulted from breeding a founder pair. Alternatively, the foundation colony is first expanded to produce sufficient numbers of distinct brother-sister pairs and ES cells may then be obtained from embryos resulted from breeding these brother-sister pairs.

ES cells may be cryopreserved using method known to those skilled in the art. See, for example, Hogan et al., 2003.

Cryopreserved ES cells of the pedigree-tracked stock can be thawed and used to re-establish a foundation colony at appropriate intervals. In one embodiment, ES cells derived from a male and a female (brother-sister) embryo are introduced separately into a morula or blastocyst stage embryo and allowed to participate in the development of the animal. The resulting offspring are typically chimeras, with portions of the chimera developed from either host embryo or the contributing male or female ES cells. The germline of the chimera could contain derivatives of both the host and the contributing ES cells. By the use of coat color and/or other genetic markers, one can select offspring which are completely derived from the ES cells used. The resulting offspring can then be used to re-establish the foundation colony.

In an alternative embodiment, male ES cells and female ES cells of the pedigree-tracked stock are separately aggregated with a tetraploid host embryo (tetraploid embryo complementation), which may be made by fusion of the two cell stage embryos with, for example, an electrical pulse. Such ES cells will successfully fully colonize the mouse embryo, while the extra embryonic tissue is supplied by the tetraploid host. This will give rise to offspring that are completely derived from either the male ES cells or the female ES cells, depending on the ES cells used to aggregate with the tetraploid host embryo. Appropriate monitoring of the process using coat color and/or other genetic markers can distinguish any possible host-embryo-derived offspring from those derived from the ES cells. One can thus select offspring derived completely from each ES cell. A brother-sister pair may then be selected from the offspring derived from the male ES cell (brother) and the offspring from the female ES cell (sister) to re-establish the foundation colony.

Such techniques are known in the art. See, for example, Hogan et al., 2003. Derivation of completely cell culture-derived mice from early-passage embryonic stem cells, Proc Natl Acad Sci USA. 90, 8424-8428. See also www.mshri.on.ca/nagy/diploid/diploid.htm, and www.mshri.on.ca/nagy/Tetraploid/tetra.htm In a further embodiment, male and female offspring can be produced from a single male ES cell line of the pedigree-tracked stock. The male ES cells contain an X chromosome and a Y chromosome (XY). It has been shown that Y chromosome is lost at a high frequency in subclones of the XY cell lines, making it routine to identify XO cells in the subclones of the XY ES cell line. These XO ES cells can be used to produce female offspring that are fertile via either tetraploid embryo complementation or chimera formation (See Eggan et al., 2002). One of the female offspring can be selected to breed with one of the male offspring derived from the male ES cells (XY) to re-establish the foundation colony.

ES cells are known to be able to form germ cells in vitro. See Toyooka, Y. et al., 2003. Thus, in another embodiment, ES cells of the pedigree-tracked stock are used to give rise to germ cells in vitro, which are then used to give rise to offspring derived from the ES cells.

Another aspect of the present invention relates to methods of producing a pedigree-tracked stock of cryopreserved ES cells derived from a foundation colony.

A further aspect of the present invention relates to methods of maintaining genetic stability of an inbred mouse strain. The methods include five steps: (1) from a pedigree-tracked cryopreserved ES cells stock derived from the foundation colony of the inbred strain, selecting cryopreserved ES cells that are obtained from a single brother-sister pair and producing live animals from these ES cells; (2) from the live animals so produced, selecting a brother-sister pair as a new founder pair; and (3) repeating steps (1)-(2) at appropriate intervals.

Another aspect of the present invention provides pedigree-tracked stocks of cryopreserved ES cells derived from a foundation colony. Such pedigree-tracked stock may be used to re-establish the foundation colony at appropriate intervals.

A further aspect of the present invention provides a business method of supplying non-human animal inbred strain with limited genetic drift. The method comprises: (1) maintaining a foundation colony of the inbred strain; (2) producing a pedigree-tracked stock of cryopreserved ES cells derived from the foundation colony; (3) at an appropriate time, select cryopreserved ES cells that are obtained from a single brother-sister pair, and produce live animals from them; (4) out of the live animals produced, select a brother-sister pair and use them as a new founder pair to derive future animals in the strain; (5) repeating steps (1) to (4) at appropriate intervals; and providing an animal in response to the customer's order.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999, Manipulating the Mouse Embryos, A Laboratory Manual, $3^{rd}$ Ed., by Hogan et al., Cold Spring Harbor Laboratory Press, Cold Spring Harbor, N.Y., 2003, Gene Targeting: A Practical Approach, IRL Press at Oxford University Press, Oxford,1993, and Gene Targeting Protocols, Human Press, Totowa, N.J., 2000. All patents, patent applications and references cited herein are incorporated in their entirety by reference.

Maintaining the Genetic Stability of Congenic Mouse Strain

Congenic rodent strains are known in the art and generated by repeated backcrosses to an inbred (background) strain, with selection for a particular marker from the donor strain (Snell 1978, Flaherty 1981). This particular marker can be for example one or more specific DNA sequences or one or more specific genes. When more than one particular marker is backcrossed to an inbred (background) strain, then such congenics are also called double congenics or triple congenics etc. Seven backcrosses (N7) to an inbred strain result in a contribution of about 99.2% of the inbred strain and ten backcrosses (N10) in about 99.9% background contribution. Usually 10 backcrosses are considered sufficient to call a mouse strain congenic (Flaherty 1981; Silver 1995).

Alternatively, an approach called "speed congenics" can be applied. In this approach the breeding is assisted with markers selected from the inbred (background) rodent strain (Markel et al., 1997; Wakeland et al., 1997). Using an appropriate marker selected for the inbred (background) strain in addition to the donor strain marker (the congenic marker), four backcrosses (N4) to the inbred strain yield about 99% of the inbred strain and five backcrosses (N5) result in essentially 100% background contribution. Appropriate markers are such which allow to distinguish one rodent inbred strain from another rodent inbred strain and a number of such marker panels have been established and are known in the art. For inbred marker selection for example single-nucleotide-polymorphism (SNP) or DNA microsatellite markers (SSLP markers) are commonly used (Goto et al. 2005). Petkov et al. 2004 has described 240 different SNP markers to differentiate 48 different inbred mouse strains (Petkov et al. 2004, Genomics Vol. 83, p. 902-911) and then further developed 1638 SNP markers to distinguish 102 different mouse inbred strains (Petkov et al. 2004, Genome Research, Vol. 14, p. 1806-1811). In mice, 3 markers per chromosomes are considered sufficient for speed congenic approaches (Goto K, Ebukuro M, Itoh T. 2005; Comp Med 55:34-36) Similar for rat inbred mice, single-nucleotide-polymorphism and microsatellite marker panels are known and used for speed congenic applications (Hirano et al. 2006, CancerLetters, Vol. 231, p. 185-1911). For the rat Bryda and Riley describe 87 microsatellite markers (also know as simple sequence length polymorphisms or SSLP) to distinguish rat inbred strains, which can be applied for speed congenic breeding approaches (Bryda and Riley 2008, J Am Assoc Lab Anim Sci. 47(3): 37-41). 5000; SSLP markers have been described to distinguish 48 rat strains (Klöting I, Voigt B, Kovacs P. 1997, Mamm Genome 8:589-59; de la Cruz N, Bromberg S, Pasko D, Shimoyama M, Twigger S, Chen J, Chen C F, Fan C, Foote C, Gopinath G R, et al. 2005, Nucleic Acids Res 33:D485-D491). Other methods like sequencing, PCR or proteomic approaches may be used to select and test markers for the background inbred strain.

Congenic mouse strains are, for example, but not limited to B6.129P2-Apoetm1Unca (The Jackson Laboratory Stock number 002052); B6.129P2-Apoetm1Unc; B6.129-Gt (ROSA)26Sortm1Luo/J; B6.PL-Thy1a/CyJ; C.Cg-Tg (DO11.10)10D1o/J; B6.129S7-Rag1tm1Moma; NOD.Cg-Prkdcscid Il2rgtm1Wj1/SzJ; CBySmn CB17-Prkdcscida; B6.SJL-Ptprca Pepcb/BoyJ; B6.129S7-Ld1rtm1Her/J; B6.BKS(D)-Leprdb/J; B6.V-Lepob/J; B6.129S7-Ifngtm1Ts/J; B10.RIII-H2r H2-T18b/(71NS)SnJ; B6.129X1-Fcgrttm1Dcr/Dcd; B6.129P2-Nos3tm1Unc/J; B6.129P2-Psen1tm1V1n/J; C.129S4(B6)-Fcgr2btm1TtK/cAnNTac; B6.129S4-Fcgr2btm1TtK; B6.SJL(129S6)-Ptprca/Boy-CrTac-Rag2tm1Fwa. (see The Jackson Laboratory, Taconic and Charles River Laboratories website for further listings)

Example for congenic rat strains are, but not limited to SS.BN-(D13Rat7-D13Rat88)/Mcwi; SS.BN-(D13Rat111-D13Rat127)/Mcwi; SS.BN-(D13Rat111-D13Got22)/Mcwi; WKY.SHRSP-(D1Rat200-D1Rat216)(Shbg-Atp1b2)/Bbb; SS.BN-(D13Rat178-D13Got45)/Mcwi; WKY.SHRSP-(D1Rat200-D1Rat216)(Shbg-Atp1b2)/Bbb; SS.BN-(D13Rat123-D13Rat101)/Mcwi; WKAH.LEC-Atp7bhts/Tj; DA.PVG.1AV1-(D4Rat155-D4Rat84); F344.OLETF-(D14Rat23-D14Rat12)(D8Rat54-D8Mgh17)/Tj (for example see the Rat Genome Database (RGD) website for additional congenic rat strains—at rgd.mcw.edu)

V. Maintaining the Genetic Stability of a Congenic Rodent Strain

One aspect of the present invention relates to methods of producing a pedigree-tracked stock of cryopreserved animal embryos derived from a foundation colony, by breeding at least one congenic founder pair. The founder pair is a brother-sister or parent-offspring pair. Embryo production may be by mating (copulation) or by in vitro or in vivo artificial means. Artificial means include, but are not limited to, assisted reproductive techniques, such as artificial insemination, surgical assisted artificial insemination, in vitro fertilization of in vitro or in vivo matured oocytes, follicles, spermatogonial stem cells, germ cells or primordial cells; intracytoplasmic sperm injection, intracytoplasmic spermatid injection, cloning, embryo electrofusion of oocytes with spermatids and the like.

The cryopreserved embryos may be stored by methods known to those skilled in the art. In one embodiment, cryopreserved embryos are stored in sterile plastic insemination straws. Each straw contains only sibling embryos. A straw may contain only one embryo or it may contain multiple sibling embryos. Alternatively, cryopreserved embryos may be stored in other appropriate containers such as plastic vials or glass ampoules.

Pre-Gametes May be Matured Into Gametes in vitro or in vivo.

Another aspect of the present invention includes (1) backcrossing a congenic founder female or male to the appropriate background inbred strain (for example a B6.congenic mouse is backcrossed to the C57BL/6 inbred mouse strain). In one embodiment, the congenic founder female or male is backcrossed to a pedigreed background inbred strain; the breeding partner is selected from an inbred foundation colony. The backcross is performed at least once (F1), or twice (N2), three times (N3), four times (N4), five times (N5), six times (N6), seven times (N7) or more. One of the backcrosses may include breeding with a male mouse of the pedigreed inbred strain to introduce the Y chromosome of the pedigreed inbred strain, unless the congenic marker is located on the Y chromosome; (2) intercrossing the backcrossed congenic rodents by selecting a brother-sister (or parent-offspring pair) obtained in step (1) to produce rodents homozygous for the congenic marker, to establish the congenic foundation colony; (3) obtaining pedigree-tracked rodent embryos by brother-sister or parent-offspring breeding of congenic foundation rodents obtained in step (2) and cryopreserving the pedigree-tracked rodent embryos; (4) producing live rodents from cryopreserved rodent embryos obtained in step (3); (5) re-establishing the foundation colony by selecting a pedigreed congenic breeding pair from the live rodents obtained in step (4) and breeding them to produce offspring, wherein the congenic breeding pair is a brother-sister or a parent-offspring pair from which all subsequent rodents of the strain are derived; (6) replenishing the foundation colony by repeating steps (4) to (5) at intervals of 1 to 20 generations and thus, inhibiting the accumulation of genotypic changes, thereby maintaining genetic stability of the congenic rodent strain.

Another aspect of the present invention includes (1) backcrossing of the congenic founder female or male to the appropriate background inbred strain (for example, a B6.congenic mouse is backcrossed to the C57BL/6 inbred mouse strain). In one embodiment the congenic founder female or male is backcrossed to a pedigreed background inbred strain with the breeding partner being selected from an inbred foundation colony. The backcross is performed at least once (F1), or twice (N2), three times (N3), four times (N4), five times (N5), six times (N6), seven times (N7) or more. One of the backcrosses may include breeding with a male mouse of the pedigreed inbred strain to introduce the Y chromosome of the pedigreed inbred strain, unless the congenic marker is located on the Y chromosome; (2) intercrossing the backcrossed congenic rodents by selecting a brother-sister or parent-offspring pair obtained in step (1) to produce rodents homozygous for the congenic marker to establish the congenic foundation colony; (3) obtaining pedigree-tracked gametes or pre-gametes of the congenic foundation rodents obtained in step (2) and cryopreserving the pedigree-tracked pedigree-tracked gametes or pre-gametes ; (4) producing live rodents from cryopreserved rodent gametes or pre-gametes obtained in step (3) by breeding gametes and/or pre-gametes; (5) re-establishing the foundation colony by selecting a pedigreed congenic breeding pair from the live rodents obtained in step (4) and breeding them to produce offspring, wherein the congenic breeding pair is a brother-sister or a parent-offspring pair from which all subsequent rodents of the strain are derived; (6) replenishing the foundation colony by repeating steps (4) to (5) at intervals of 1 to 20 generations and thus, inhibiting the accumulation of genotypic changes, thereby maintaining genetic stability of the congenic rodent strain.

Another aspect of the present invention includes (1) selecting a congenic founder male and cryopreserving or freeze drying the male gametes or pre-gametes, thereby establishing a male founder pedigree-tracked gamete or pre-gamete stock; (2) breeding the male gametes or pre-gametes obtained in step (1) to females from a pedigreed background inbred foundation stock to obtain live offspring; (3) optionally, breeding the offspring obtained in step (2) to the background inbred foundation stock, one or more times; (4) intercrossing the backcrossed congenic rodents by selecting a brother-sister or parent-offspring pair obtained in step (2) or (3) to produce rodents homozygous for the congenic marker to establish the congenic foundation colony; (5) re-establishing the foundation colony by selecting a pedigreed congenic breeding pair from the live rodents obtained in step (4) and breeding them to produce offspring, wherein the congenic breeding pair is a brother-sister or a parent-offspring pair from which all subsequent rodents of the strain are derived; (6) replenishing the foundation colony by repeating steps (2) to (5) at intervals of 1 to 20 generations and thus, inhibiting the accumulation of genotypic changes, thereby maintaining genetic stability of the congenic rodent strain. In some embodiments, the offspring obtained in step (2) are bred to the background inbred foundation stock one or more times.

Another aspect of the present invention includes (1) selecting a congenic founder male and cryopreserving or freeze drying the female gametes or ovaries, thereby establishing a female founder pedigree-tracked gamete or pre-gamete stock; (2) breeding the female gametes or pre-gametes obtained in step (1) to males from a pedigreed background inbred foundation stock to obtain live offspring; (3) optionally, breeding the offspring obtained in step (2) to the background inbred foundation stock, one or more times; (4) intercrossing the backcrossed congenic rodents by selecting a brother-sister or parent-offspring pair obtained in step (2) or (3) to produce rodents homozygous for the congenic marker to establish the congenic foundation colony; (5) re-establishing the foundation colony by selecting a pedigreed congenic breeding pair from the live rodents obtained in step (4) and breeding them to produce offspring, wherein the congenic breeding pair is a brother-sister or a parent-offspring pair from which all subsequent rodents of the strain are derived; (6) replenishing the foundation colony by repeating steps (2) to (5) at intervals of 1 to 20 generations and thus, inhibiting the accumulation of genotypic changes, thereby maintaining genetic stability of the congenic rodent strain. In some embodiments, the offspring obtained in step (2) are bred to the background inbred foundation stock one or more times.

Some aspects of the invention include (1) selecting a congenic founder female and cryopreserving the female gametes or pre-gametes to establish the female founder pedigree-tracked gamete or pre-gamete stock; (2) breeding the female gametes or pre-gametes obtained in step (1) one or more times to males from a pedigreed background inbred foundation stock to obtain live offspring; (3) intercrossing the backcrossed congenic rodents by selecting a brother-sister or parent-offspring pair obtained in step (2) to produce rodents homozygous for the congenic marker to establish the congenic foundation colony; (4) re-establishing the foundation colony by selecting a pedigreed congenic breeding pair from the live rodents obtained in step (3) and breeding them to produce offspring, wherein the congenic breeding pair is a brother-sister or a parent-offspring pair from which all subsequent rodents of the strain are derived; (5) replenishing the foundation colony by repeating steps (2) to (4) at intervals of 1 to 20 generations and thus, inhibiting the accumulation of genotypic changes, thereby maintaining genetic stability of the congenic rodent strain.

REFERENCES

Flaherty L. 1981. Congenic strains. In The Mouse in Biomedical Research, Vol. 1, Foster H L, Small J D, Fox J G (eds.), Academic Press, New York, pp. 215-222.

Markel P, Shu P, Ebeling C, Carlson G A, Nagle D L, Smutko J S, Moore K J. 1997. Theoretical and empirical issues for marker-assisted breeding of congenic mouse strains. Nat Genet. 17:280-284.

Silver L M. 1995. Mouse Genetics: Concepts and Applications. Oxford University Press, Oxford.

Snell G D. 1978. Congenic resistant strains of mice. In Origins of Inbred Mice, Morse H C (ed.), Academic Press, New York, pp. 1-31.

Wakeland E, Morel L, Achey K, Yui M, Longmate J. 1997. Speed congenics: a classic technique in the fast lane (relatively speaking). Immunol Today 18: 472-477.

Goto K, Ebukuro M, Itoh T. 2005 Microsatellite-directed selection of breeders for the next backcross generation by using a minimal number of loci. Comp Med. 2005, 55(1):34-6

Klöting I, Voigt B, Kovacs P. 1997. Comparison of genetic variability at microsatellite loci in wild rats and inbred rat strains (*Rattus norvegicus*). Mamm Genome 8:589-59.

De la Cruz N, Bromberg S, Pasko D, Shimoyama M, Twigger S, Chen J, Chen C F, Fan C, Foote C, Gopinath G R, et al. 2005. The Rat Genome Database (RGD): developments towards a phenome database. Nucleic Acids Res 33:D485-D491.

EXAMPLES

The invention now being generally described will be more readily understood by reference to the following examples, which are included merely for purposes of illustration of certain aspects and embodiments of the present invention, and are not intended to limit the invention.

Example 1

Maintaining the Genetic Stability of an Inbred Strain Using Embryo Stock

FIG. 1 depicts a scheme for creating a pedigree-tracked stock of cryopreserved embryos derived from a foundation colony to be used to maintain genetic stability. This is only one embodiment of the present invention. The left panel in the Figure shows the first step: a founder pair (the P generation) is selected and bred several times to generate multiple litters. In the scheme represented, six sisters and two brothers (F1 generation) are picked for the next step. The middle panel of the Figure shows the second step: Each F1 generation sister is separately caged in order for their litters to be tracked. In the scheme shown, the same male is mated in rotation with a group of three F1 generation sisters. Each of the six F1 generation sisters will be mated multiple times with their respective brother to produce multiple litters of F2 generation. The right panel of the Figure shows the third step: nine F2 generation sisters and one brother derived from a single F1 generation sister will be used in IVF to produce embryos. IVF is performed for each of the 6 or more sets of about 9 sisters and one brother. Embryos from each of the 54 females (6×9) are cryopreserved in individual straws. This will give more than two fold redundancy covering 25 years plus and includes embryos for controls and/or unforeseen eventualities.

At appropriate intervals, sibling embryos from the cryopreserved stock are thawed and transferred to a pseudopregnant female recipient to generate offspring. A brother-sister pair is then selected from the offspring as a new founder pair to re-establish the foundation colony.

A person with ordinary skill in the art will understand that what described above merely represents one embodiment for producing a pedigree-tracked cryopreserved embryo stock of the present invention. Clearly, many of the details of the scheme can vary, including, for example, the number of generations needed to expand the foundation colony before making the embryo stock, the number of females used per generation and the type of the inbred breeding pair used. For example, one may select a breeding pair and produce F(x+1) offspring (where x is the generation number at the time of selection) from the breeding pair. In the meantime, sperm from the male of the breeding pair are obtained and cryopreserved in aliquots. Female F(x+1) offspring may be bred by IVF with the thawed sperm (parent-offspring breeding) to produce F(x+2) embryos that can be cryopreserved to produce pedigree-tracked stock.

Example 2

Maintaining the Genetic Stability of an Inbred Strain Using Gametes Stock

In one embodiment, female mice derived from a foundation colony are superovulated and oocytes are collected and cryopreserved. Sperm from a respective male sibling of the females are also collected and cryopreserved. At appropriate intervals, oocytes and sperm from siblings are thawed and used to produce embryos by IVF. Resulting embryos are transferred to pseudopregnant recipients to yield offspring. A brother-sister pair is then selected from the offspring as a new founder pair to re-establish the foundation colony.

Example 3

Maintaining the Genetic Stability of an Inbred Strain Using Pre-Gametes Stock

Cryopreserved Ovaries and Sperm

Ovaries from females derived from a foundation colony are cryopreserved (see Example 5) as are sperm from their respective male siblings. At desired intervals, the ovaries are thawed and transferred. Once fertility of the recipient female has been demonstrated, she is superovulated and artificially inseminated using cryopreserved sperm from one of her siblings to produce offspring. A brother-sister pair is then selected from the offspring as a new founder pair to re-establish the foundation colony.

Cryopreserved Ovaries and Spermatogonial Stem Cells

Ovaries are collected and cryopreserved as above. (See Example 5) Spermatogonial stem cells are collected from the male siblings and cryopreserved. Spermatogonial stem cells are thawed and transplanted at appropriate intervals to produce fertile males. Once fertility of the male has been demonstrated, ovaries from his female siblings are thawed and transplanted. The animals are then mated to produce offspring. A brother-sister pair is then selected from the offspring as a new founder pair to re-establish the foundation colony. See Candy et al., 2000, and Nagano and Brinster 1998.

Example 4

Maintaining the Genetic Stability of an Inbred Strain Using ES Cell Stock

Male and female ES cells are isolated from an inbred, pedigreed bother-sister mating and cryopreserved. At appropriate interval, the male and female ES cells derived from a brother-sister mating are recovered from storage. Host embryos are prepared from a genetically different strain, e.g. different coat color from the ES cells, and induced to fuse via an electrical pulse yielding a tetraploid embryo. The surviving embryos are cultured to morula stage. Multiple groups of male ES cells (1-40 cells) are placed in close proximity to one of the tetraploid host embryos. Likewise, multiple groups of female ES cells (1-40 cells) are placed in close proximity to the other tetraploid host embryo. After the ES cells and their respective tetraploid embryo have coalesced to a single embryo (overnight culture), the embryos are introduced into a pseudopregnant female recipient. After birth appropriate coat color and/or other genetic markers can be used to select offspring that are derived from the ES cells. Brother-sister pairing can then be made using these offspring to re-establish the foundation colony.

Example 5

Ovary Cryopreservation and Thawing

Cryopreservation

Ovaries can be harvested from female mice as young as 4 days (see Carroll and Gosden 1993, *Human Reproduction* vol 8, pp 1163-1167). Female mice are euthanized and ovaries are dissected out of the bursa membrane. The ovaries are transferred into 1 ml of M2 medium (Specialty Media Cat#MR-015-R) at room temperature or colder (up to +4° C.) and remove excess tissue or fat from ovaries if necessary. Ovaries are washed in 1 ml M2 medium. Then ovaries can be split into fragments (from 2 to 32 fragments per ovary).

For cryopreservation the ovary fragments are transferred using forceps into a ovary cryopreservation medium consisting of 10% fetal bovine serum (FBS), 1.5 M DMSO in M2 medium at room temperature. The ovaries are incubated for 10 min at room temperature. Then straws are loaded. For whole or bisected ovaries ½ cc straws (IMV; Maple Grove, Minn.) are used, for smaller fragments (⅓, ¼ up to ¹⁄₁₆) ½ cc straws (IMV; Maple Grove, Minn.) are used.

For loading aspirate the straw with ovary cryopreservation medium (10% FBS, 1.5 M DMSO, M2 medium) up to the 3 cm mark, then aspirate air up to the 2 cm mark, then aspirate the ovary or ovary fragment in ovary cryopreservation medium to the next 2 cm mark, aspirate air until the plug is saturated with ovary cryopreservation medium. Seal straw with critoseal (Fisher Scientific 02-676-20) or an impulse heat sealer. Place straws into a Biocool alcohol freezer (Minitube 16820/1803) at −7° C. Incubate for 5 min then seed (i.e. induce ice formation) straw by touching liquid nitrogen cooled forceps to the top of the column of medium containing ovary. After 5 min check each straw for seeding and start freezing at 0.5° C. per min down to −30° C., then freeze rapidly by plunging straws directly into liquid nitrogen, then transfer into cassettes and store in liquid nitrogen.

Thawing

For thawing remove straw from liquid nitrogen, and hold in air until thawed. The contents of the straw are emptied into a Petri dish and the ovary or ovary fragment is picked up with forceps and put into a 1 mL drop of M2 medium. Then ovary or ovary fragment is transferred once into fresh M2 until transplantation.

Example 6

Balb/cByJ Serial Ovary Transplant, Fresh

5 Balb/cByJ mice, 3 month old, are superovulated using 5 IU PMSG between 5 and 6 pm, followed by 5 IU hCG (human chorionic gonadotropin) 48-49 h post-PMSG. The mice are euthanized and ovaries are dissected out and the bursa membrane is removed. The ovaries are transferred into 1 ml of M2 medium (Specialty MediaMR-015-R) at room temperature or colder (up to +4° C.) and excess tissue or fat is removed. The ovaries are washed in 1 ml M2 medium and split into two fragments per ovary. The ovaries are incubated in M2 medium until the transplantation. In vivo mature oocytes are also collected from the ampulla region of the oviducts.

The average number of isolated oocytes per female was 21 from 5 out of 5 females ovulating. The oocytes are used in an in vitro fertilization experiment using frozen BALB/cByJ sperm ($1^{st}$ IVF). The successful fertilization is shown in FIG. 2, with 37% (37/107) fertilization rate. FIG. 2 is a bar graph that shows the average number of oocytes that were isolated and the fertilization rates after serial transfer of fresh BALB/cByJ ovaries. For the 1st superovulation, the females were intact with two ovaries and had not undergone surgery. In the 2nd and 3rd superovulation groups, each female had had two ovary halves transplanted (equivalent to 1 whole ovary). The data presented for these two groups is the average number of oocytes isolated per female multiplied by 2 (for comparison with females with two ovaries).

For the first transplantation 5 (C57BL/6J-Tg(UBC-GFP)30Schaa x Balb/cByJ)F1 mice (host), virgin 6-14 weeks old, were anesthetized. Host ovaries are removed immediately before transplantation. A single ovary fragment is transplanted (first transplant) to each of the ovarian bursa of the host. A total of 10 ovary fragments were transplanted into 5 host virgin females. To assess the success of transplantation, the host females were superovulated 11 days after transplantation and oocytes were collected.

The oocytes were used in an in vitro fertilization experiment using frozen BALB/cByJ sperm ($2^{nd}$ IVF). The successful fertilization is shown in FIG. 2, with 7% (2/30) fertilization rate.

At the time of oocyte collection, the ovary fragments were collected as described above and immediately (or within 1 h) transplanted (second transplant) into 3 (C57BL/6J-Tg(UBC-GFP)30Scha/J x Balb/cByJ)F1 mice (host), virgin 6-14 weeks old, as described above. A single ovary fragment was transplanted to each of the ovarian bursa of the host. A total of 6 ovary fragments were transplanted into 3 host virgin females. To assess the success of transplantation, the host females are superovulated 11 days after transplantation and oocytes are collected.

The oocytes were used in an in vitro fertilization experiment using sperm from frozen BALB/cByJ (3rd IVF). The successful fertilization is shown in FIG. 2, with 100% (5/5) fertilization rate.

Example 7

Balb/cByJ Serial Ovary Transplant, Frozen

5 Balb/cByJ mice, 4 month old, virgin, are superovulated using 5 IU PMSG between 5 and 6 pm, followed by 5 IU hCG 48-49 h post-PMSG.

The mice are euthanized and ovaries are dissected out and the bursa membrane is removed. The ovaries are transferred into 1 ml of M2 medium (Specialty MediaMR-015-R) at room temperature or colder (up to +4° C.) and excess tissue or fat is removed. Oocytes are also collected before the ovaries are frozen.

In this example the average number of isolated oocytes per female was 26 from 5 out of 5 females ovulating. The oocytes were used in an in vitro fertilization experiment using frozen BALB/cByJ sperm ($1^{st}$ IVF). The successful fertilization is shown in FIG. 3, with 5% (4/77) fertilization rate. FIG. 3 is a bar graph that shows the average number of oocytes that were isolated and the fertilization rates after serial transfer of frozen BALB/cByJ ovaries. For the 1st superovulation, the females were intact with two ovaries and had not undergone surgery. In the 2nd and 3rd superovulation groups, each female had had two ovary halves transplanted (equivalent to one whole ovary). The data presented for these two groups is the average number of oocytes isolated per female multiplied by 2 (for comparison with females with two ovaries).

The ovaries are washed in 1 ml M2 medium and split into two fragments per ovary. The ovaries are cryopreserved as described in Example 5 and according to Manipulating the Mouse Embryo; A Laboratory Manual (Nagy, Gertsenstein, Vintersten, Behringer, Cold Spring Harbor Laboratory Press; 3 edition, 2002).

For transplantation 5 (C57BL/6J-Tg(UBC-GFP)30Scha/J x Balb/cByJ)F1 mice (host), virgin 6-14 weeks old, were anesthetized. Host ovaries were removed immediately before transplantation. The ovary fragments were thawed as described in Example 5. A single ovary fragment was transplanted (first transplant) to each of the ovarian bursa of the host (for detailed description see Manipulating the Mouse Embryo; A Laboratory Manual (Nagy, Gertsenstein, Vintersten, Behringer, Cold Spring Harbor Laboratory Press; 3 edition, 2002). A total of 10 ovary fragments were transplanted into 5 host virgin females. To assess the success of transplantation, the host females were superovulated 11 days after transplantation and oocytes were collected.

The oocytes were used in an in vitro fertilization experiment using sperm from frozen BALB/cByJ(2nd IVF). The successful fertilization is shown in FIG. 3, with 60% (12/20) fertilization rate.

At the time of oocyte collection, the ovary fragments were collected as described above and immediately (or within 1 hour) transplanted (second transplant) into 3 (C57BL/6J-Tg(UBC-GFP)30Scha/J x Balb/cByJ)F1 mice (host), virgin 6-14 weeks old, as described above. A single ovary fragment was transplanted to each of the ovarian bursa of the host. A total of 6 ovary fragments were transplanted into 3 host virgin females. To assess the success of transplantation, the host females were superovulated 11 days after transplantation and oocytes were collected.

The oocytes were used in an in vitro fertilization experiment using sperm from frozen BALB/cByJ (3rd IVF). The successful fertilization is shown in FIG. 3, with 89% (8/9) fertilization rate.

Example 8

C57BL/6J Serial Ovary Transplant, Fresh

5 C57BL/6J female mice, 10 weeks old, virgin are superovulated using 5 IU PMSG between 5 and 6 pm, followed by 2.5 IU hCG 48-49 h post-PMSG. The females are euthanized and ovaries are dissected out and the bursa membrane, oviduct, and fat are removed. In vivo mature oocytes are also collected from the ampulla region of the oviducts.

The average number of isolated oocytes per female was 13 (see FIG. 4, "$1^{st}$ Superovulation") from 4 out of 5 females ovulating. The oocytes are used in an in vitro fertilization experiment using fresh sperm from C57BL/6J ($1^{st}$ IVF). The successful fertilization is shown in FIG. 5, with 80.4% (41/51) fertilization rate. The ovaries are transferred into 1 ml of M2 medium (Specialty MediaMR-015-R) at room temperature or colder (up to +4° C.) and excess tissue or fat is removed. The ovaries are washed in 1 ml M2 medium and split into two fragments per ovary. The ovaries are held in M2 medium until transplantation at room temperature.

For the first transplantation 9 C57BL/6J-Tg(UBC-GFP)30Scha/J-/- (JR4353) mice (host), virgin 5 weeks old, were anesthetized by intraperitoneal injection of tribromoethanol (0.2 mL/10 g body weight). Host ovaries were removed immediately before transplantation. A single ovary fragment was transplanted to each of the ovarian bursa of the host, i.e. two half ovaries into each host. A total of 18 ovary fragments were transplanted (first transplant) into 9 host virgin females. To assess the overall success of transplantation, the host females were superovulated 18 days after transplantation and oocytes were collected. It was observed that 17 ovary fragments transplanted successfully. The average number of isolated oocytes per female was 18 for successful transplants (see FIG. 4, "$2^{nd}$ Superovulation"). FIG. 4 is a bar graph that shows the average number of oocytes that were isolated after serial ovary transplantation of fresh C57BL/6J ovaries. For the 1st superovulation, the females were intact with two ovaries and had not undergone surgery. In the 2nd and 3rd superovulation groups, each female had had two ovary halves transplanted (equivalent to one whole ovary). The data presented for these two groups is the average number of oocytes isolated per female multiplied by 2 (for comparison with females with two ovaries).

The oocytes were used in an in vitro fertilization experiment using fresh sperm from C57BL/6J (2nd IVF). The successful fertilization is shown in FIG. 5, with 80.3% (57/71) fertilization rate.

At the time of oocyte collection, the ovary fragments are collected as described above and immediately (or within 1 hour) transplanted (second transplant) into 9 C57BL/6J-Tg(UBC-GFP)30Scha/J-/- mice (host), virgin 5 weeks old, as described above. A single ovary fragment is transplanted to each of the ovarian bursa of the host. A total of 17 ovary fragments are transplanted into 9 host virgin females. To assess the success of transplantation, the host females are superovulated 18 days after transplantation and oocytes were collected. 17 ovary grafts transplanted successfully. The average number of isolated oocytes per female was 8 for successful transplants (see FIG. 4).

The oocytes were used in an in vitro fertilization experiment using sperm from C57BL/6J ($3^{rd}$ IVF). The successful fertilization is shown in FIG. 5, with 76.5% fertilization rate.

At the time of oocyte collection, the ovary fragments were collected as described above and transplanted (third transplant) within one hour into 5 C57BL/6J-Tg(UBC-GFP)30Scha/J-/- mice (host), virgin 5 weeks old, as described above. A single ovary fragment was transplanted to each of the ovarian bursa of the host. A total of 7 ovary fragments were transplanted into 5 host virgin females. To assess the success of transplantation, the host females were superovulated 18 days after transplantation and oocytes were collected. The average number of isolated oocytes per female was 8 for successful ovulating females (see FIG. 4).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The methods, embryo stocks, gamete stocks and pre-gamete stocks are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

It should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Example 9

Ovary Fragmentation

Ovaries are isolated from a rodent inbred strain, for example from mouse BALB/cByJ and dissected into 16 (FIG. 6) or 32 fragments (FIG. 7). The fragments can be frozen individually or in groups per ovary until used for transplantation. Typically, excess tissue and/or fat and/or the bursa membrane are removed before dissecting. Alternatively, the fragments are transplanted directly into compatible host females. Usually one or two fragments are transplanted into one host female.

Example 10

Ovary Fragmentation and Transplantation

In this example C57BL/6J (B6; The Jackson Laboratory Stock Number 000664) and B6(Cg)-Tyrc-2J/J (B6 albino; The Jackson Laboratory Stock Number 000058) female mice were used as ovary donor and ovary recipients.

Females are euthanized and ovaries are dissected out and the bursa membrane, oviduct, and fat are removed. Ovaries are transferred into 1 ml of M2 medium (Specialty MediaMR-015-R) and held between 4° C. and ambient temperature (up to 25° C.). Each ovary is cut into 2, 4, 8 or 16 fragments, and either frozen or directly transplanted fresh into ovariectomized compatible host females.

For example, C57BL/6J donor ovaries are cut into 2 or 4 fragments and cryopreserved. The thawed fragments are transplanted into ovariectomized B6(Cg)-Tyrc-2J/J (B6 albino) host females, one fragment per female. As shown in table 1, about the same number of offspring can be obtained when using ¼ of an ovary or ½ of an ovary. An average of 3.5 pups/litter are produced from the ½ ovaries compared to 3 pups/litter for the ¼ ovaries transplantations.

For example, B6(Cg)-Tyrc-2J/J (B6 albino) are cut into 2, 4, 8 or 16 fragments and directly transplanted into ovariectomized C57BL/6J recipient females, one fragment per female. In all cases live offspring are obtained. The litter size ranged from 3 to 4.7 pups/litter.

TABLE 1

Live born Mice after Transplantation of Ovary fragments

| Ovary Fraction | Fresh or Frozen | Host Strain | Donor Strain | Number of Hosts | Number of litters | Number of pups | Pups/Litter |
|---|---|---|---|---|---|---|---|
| ½ | Frozen | C57BL/6J | B6 albino | 4 | 11 | 38 | 3.5 |
| ¼ | Frozen | C57BL/6J | B6 albino | 4 | 11 | 33 | 3.0 |
| ½ | Fresh | B6 albino | C57BL/6J | 4 | 7 | 24 | 3.4 |
| ¼ | Fresh | B6 albino | C57BL/6J | 4 | 16 | 48 | 3.0 |
| ⅛ | Fresh | B6 albino | C57BL/6J | 4 | 3 | 10 | 3.3 |
| 1/16 | Fresh | B6 albino | C57BL/6J | 4 | 3 | 14 | 4.7 |

REFERENCES

Candy C J, Wood M J, Whittingham D G. 2000. Restoration of a normal reproductive lifespan after grafting of cryopreserved mouse ovaries. Hum Reprod. June; 15(6):1300-4.

Chiu et al., Effects of Myo-inositol on the in-vitro Maturation and Subsequent Development of Mouse Oocytes, Human Reprod. 18: 408-416 (2003)

Eggan, K. et al. (2002). "Male and female mice derived from the same embryonic stem cell clone by tetraploid embryo complementation." Nat Biotechnol 20(5): 455-9.

Glenister and Hall, "Cryopreservation and rederivation of embryos and gametes" in Mouse Genetics & Transgenics: A Practical Approach, 2nd Edition (I Jackson & C Abbott, eds.) Oxford Univ. Press, Oxford, pp. 27-59.

Han M S; Niwa K; Kasai M, Vitrification of rat embryos at various developmental stages.

Theriogenology 2003 Apr. 15; 59(8):1851-63

Hogan, B., Beddington, R., Costantini, F., Lacy, E. Manipulating the Mouse Embryos, A Laboratory Manual, 3rd Ed., Cold Spring Harbor Laboratory Press, Cold Spring Harbor, N.Y., 2003, Hubner et al., Derivation of oocytes from mouse embryonic stem cells, Science 300: 1251-6 (2003).

Kimura and Yanagimachi, Intracytoplasmic sperm injection in the mouse, Biol. Reprod. 52: 709-20, 1995.

Kimura and Yanagimachi, Development of normal mice from oocytes injected with secondary spermatocyte nuclei, Biol. Reprod. 53: 855-62, 1995

Kimura and Yanagimachi, Mouse oocytes injected with testicular spermatozoa or round spermatids can develop into normal offspring, Development 121: 2397-405, 1995.

Kubota, Avarbock and Brinster, Spermatogonial stem cells share some, but not all, phenotypic and functional characteristics with other stem cell, Proc. Nat. Acad. Sci. 100: 6487-6492, 2003.

Lavoir et al., Isolation and identification of germ cells from fetal bovine ovaries. Molecular Reprod. Dev. 37: 413-424 (1994).

Nagano M, Brinster R L. 1998. Spermatogonial transplantation and reconstitution of donor cell spermatogenesis in recipient mice. APMIS. January; 106(1):47-55; discussion 56-7.

Nagy, A.; Rossant, J.; Nagy, R.; Abramownewerly, W.; Roder, J. C. (1993). Derivation of completely cell culture-derived mice from early-passage embryonic stem cells, Proc Natl Acad Sci USA. 90, 8424-8428.

O'Brien et al., A Revised Protocol for In Vitro Development of Mouse Oocytes from Primordial Follicles Dramatically Improves Their Developmental Competence, Biol. Reprod. 68: 1682-1686 (2003).

Ogura and Yanagimachi, Spermatids as male gametes, Reprod. Fertil. Dev. 7: 158-9, 1995

Sato M, Kimura M. 2002.Comparison of intrabursal transfer of spermatozoa, a new method for artificial insemination in mice, with intraoviductal transfer of spermatozoa.

J Assist Reprod Genet. November; 19(11):523-30.

Schroeder and Eppig 1984 Dev. Biol. 102:493

Sirard et al. 1988, Biol. Reprod. 39:546

Specht and Schoepfer, Deletion of the alpha-synuclein locus in a subpopulation of C57BL/6J inbred mice, BMC Neurosci. 2, 11 (2001).

Strelchenko, Bovine Pluripotent stem cells, Theriogenology 45: 130-141(1996)

Sztein, J M, Noble K, Farley J S, Mobraaten L E. 2001. Comparison of permeating and nonpermeating cryoprotectants for mouse sperm cryopreservation. Cryobiology 42 (1):28-39.

Sztein et al., Biol. Reprod. 58: 1071-1074 (1998)

Toyooka, Y., N. Tsunekawa, et al. (2003). Embryonic stem cells can form germ cells in vitro, Proc Natl Acad Sci USA 100(20): 11457-62.

Wolfe H G. 1967. Artificial insemination of the laboratory mouse (Mus musculus).

Lab Anim Care. 1967 August; 17(4):426-32.

Wotjak, C57Black/Box? The importance of exact mouse strain nomenclature, Trends in Genetics 19: 183-184 (2003).

Yang & Anderson, 1992, Theriogenology 38: 315-335

U.S. Pat. No. 5,758,763, entitled "Methods for Cryopreservation of Primordial Germ Cells and Germ Cells"

U.S. Application No. 20020131957, entitled "Cryopreservation of Sperm"

U.S. Pat. No. 5,160,312, entitled "Cryopreservation Process for Direct Transfer of Embryos"

WO 97/37009, entitled "Cultured Inner Cell Mass Cell-Lines Derived from Ungulate Embryos," Stice and Golueke, published Oct. 9, 1997

What is claimed is:

1. A method of maintaining genetic stability of an inbred rodent strain, comprising in the order of:
   (a) establishing a foundation colony of an inbred rodent strain, wherein the foundation colony comprises only brother-sister pairs, parent-offspring pairs or brother-sister pairs and parent-offspring pairs from which all subsequent rodents of the strain are derived;

(b) selecting at least one pedigreed inbred breeding pair as a founder pair from the foundation colony, wherein the founder pair is a brother-sister pair or a parent-offspring pair from which all subsequent rodents of the strain are derived;

(c) breeding the founder pair selected in step (b) to produce at least one female offspring;

(d) obtaining pre-gametes and/or gametes from the male of founder pair selected in (b);

(e) cryopreserving pre-gametes and/or gametes obtained in step (d), thereby producing a stock of cryopreserved pre-gametes and/or cryopreserved gametes;

(f) maintaining the stock of cryopreserved pre-gametes and/or gametes produced in step (e);

(g) obtaining rodent embryos by breeding the at least one female offspring obtained in step (c) with the cryopreserved pre-gametes or gametes of step (f) and cryopreserving the rodent embryos, thereby obtaining cryopreserved rodent embryos;

(h) producing at least one live female rodent from cryopreserved rodent embryos produced in step (g);

(i) re-establishing the foundation colony by breeding the at least one female live rodent produced in step (h) using the stock of cryopreserved pre-gametes and/or cryopreserved gametes of step (f) to produce offspring;

(j) replenishing the foundation colony by repeating steps (h) to (i) at intervals of 1 to 20 generations and thus, inhibiting the accumulation of genetic changes, thereby maintaining genetic stability of the inbred rodent strain.

2. A method of maintaining genetic stability of an inbred rodent strain, comprising in the order of:

(a) establishing a foundation colony of an inbred rodent strain, wherein the foundation colony comprises only brother-sister pairs, parent-offspring pairs or brother-sister pairs and parent-offspring pairs from which all subsequent rodents of the strain are derived;

(b) selecting at least one pedigreed inbred breeding pair as a founder pair from the foundation colony, wherein the founder pair is a brother-sister pair or a parent-offspring pair from which all subsequent rodents of the strain are derived;

(c) breeding the founder pair selected in step (b) to produce at least one female offspring;

(d) obtaining pre-gametes and/or gametes from the male of the founder pair selected in step (b);

(e) cryopreserving pre-gametes and/or gametes obtained in step (d), thereby producing a stock of cryopreserved pre-gametes and/or cryopreserved gametes;

(f) maintaining the stock of cryopreserved pre-gametes and/or gametes produced in step (e);

(g) obtaining rodent embryos by breeding the at least one female offspring obtained in step (c) with the cryopreserved pre-gametes or gametes of step (f) and cryopreserving rodent embryos, thereby obtaining cryopreserved rodent embryos;

(h) producing live rodents from cryopreserved rodent embryos obtained in step (g);

(i) re-establishing the foundation colony by selecting a pedigreed inbred breeding pair from the live rodents obtained in step (h) and breeding the inbred breeding pair to produce offspring, wherein the inbred breeding pair is a brother-sister pair from which all subsequent rodents of the strain are derived; and (j) replenishing the foundation colony by repeating steps (h) to (i) at intervals of 1 to 20 generations and thus, inhibiting the accumulation of genetic changes, thereby maintaining genetic stability of the inbred rodent strain.

3. The method of claim 1 or 2, wherein the cryopreserved pre-gametes and/or gametes in step (e) comprise cryopreserved or freeze-dried sperm, cryopreserved spermatids, cryopreserved spermatocyte, cryopreserved spermatogonia, cryopreserved spermatogonial stem cells or germ cells.

4. The method of claim 1 or 2, wherein the cryopreserved pre-gametes in step (e) are matured in vitro or in vivo to gametes.

5. A method of maintaining genetic stability of an inbred rodent strain, comprising in the order of:

(a) breeding at least one founder pair to produce at least one female offspring and at least one male offspring, wherein the founder pair is a brother-sister pair or a parent-offspring pair;

(b) obtaining rodent pre-gametes and/or gametes from the at least one female offspring and the at least one male offspring of step (a), thereby producing rodent female pre-gametes and/or gametes and rodent male pre-gametes and/or gametes;

(c) cryopreserving rodent female pre-gametes and/or gametes and rodent male pre-gametes and/or gametes obtained in step (b), thereby producing a pedigree-tracked stock of cryopreserved rodent female pre-gametes and/or gametes and cryopreserved rodent male pre-gametes and/or gametes;

(d) maintaining the stock of cryopreserved rodent female pre-gametes and/or gametes and cryopreserved rodent male pre-gametes and/or gametes produced in step (c);

(e) breeding pedigree-tracked cryopreserved female pre-gametes and/or gametes obtained in step (c) with pedigree-tracked cryopreserved male pre-gametes and/or gametes of step (c) to produce live rodents;

(f) selecting at least one pedigreed inbred breeding pair from the live rodents obtained in step (e) as a new founder pair to re-establish a foundation colony, wherein the new founder pair is a brother-sister pair, /or a parent-offspring pair from which all subsequent rodents of the strain are derived;

(g) breeding the at least one new founder pair from step (f) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (h) replenishing the foundation colony by repeating steps (e) to (g) at intervals of 1 to 20 generations and thus, inhibiting the accumulation of genetic changes, thereby maintaining genetic stability of the inbred rodent strain.

6. A method of maintaining genetic stability of an inbred rodent strain, comprising in the order of:

(a) breeding at least one founder pair to produce at least one female offspring and at least one male offspring, wherein the founder pair is a brother-sister pair or a parent-offspring pair;

(b) isolating a pedigree-tracked stock of rodent pre-gametes and/or gametes, wherein the rodent pre-gametes and/or gametes are obtained from the at least one female offspring and the at least one male offspring of step (a);

(c) breeding the pedigree-tracked stock of rodent pre-gametes and/or gametes of step (b) to produce rodent embryos, and cryopreserving the rodent embryos;

(d) producing live rodents from cryopreserved rodent embryos obtained in step (c);

(e) selecting at least one pedigreed inbred breeding pair from the live rodents obtained in step (d) as a new founder pair to re-establish a foundation colony, wherein the at least one new founder pair is a brother-sister pair, /or a parent-offspring pair from which all subsequent rodents of the strain are derived;

(f) breeding the at least one new founder pair from step (e) to produce offspring and thereby re-establish the foundation colony, wherein the foundation colony is a colony of only brother-sister pairs, only parent-offspring pairs or brother-sister pairs and parent-offspring pairs from which all subsequent rodents of the strain are derived; and (g) replenishing a foundation colony by repeating steps (d) to (f) at intervals of 1 to 20 generations and thus, inhibiting the accumulation of genetic changes, thereby maintaining genetic stability of the inbred rodent strain.

7. A method of maintaining genetic stability of an inbred rodent strain, comprising in the order of:

(a) establishing a foundation colony of an inbred rodent strain, wherein the foundation colony comprises only brother-sister pairs, parent-offspring pairs or brother-sister pairs and parent-offspring pairs from which all subsequent rodents of the strain are derived;

(b) selecting at least one pedigreed inbred breeding pair as a founder pair from the foundation colony of step (a), wherein the founder pair is a brother-sister pair/or a parent-offspring pair from which all subsequent rodents of the strain are derived;

(c) isolating at least one ovary from the founder female selected in step (b);

(d) transplanting the at least one ovary or at least one fragment of the ovary into a new host recipient;

(e) obtaining rodent embryos by breeding the host recipient obtained in step (d) with the founder male selected in step (b) and cryopreserving the rodent embryos;

(f) producing live rodents from cryopreserved rodent embryos obtained in step (e);

(g) re-establishing the foundation colony by selecting a pedigreed inbred breeding pair from the live rodents obtained in step (f) and breeding them to produce offspring, wherein the inbred breeding pair is a brother-sister pair/or a parent-offspring pair from which all subsequent rodents of the inbred strain are derived; and (h) replenishing the foundation colony by repeating steps (f) to (g) at intervals of 1 to 20 generations and thus, inhibiting the accumulation of genetic changes, thereby maintaining genetic stability of the inbred rodent strain.

8. The method of claim 5, or 6, wherein the female gametes comprise oocytes.

9. The method of claim 5, or 6, wherein the female pre-gametes comprise ovary, germ cells, oogonia, primary oocytes or secondary oocytes.

10. The method of claim 5, or 6, wherein the male gametes comprise sperm.

11. The method of claim 5, or 6, wherein the male pre-gametes comprise spermatogonial stem cell, spermatogonia, spermatid, primary spermatocyte or germ cells.

12. The method of claim 5, or 6, wherein the pre-gametes are matured in vitro or in vivo into gametes.

13. The method of claim 6, wherein the pre-gametes or gametes are cryopreserved.

14. The method of claim 5, or 6, wherein the female pre-gametes are transplanted into at least one new host recipient before breeding.

15. The method of claim 5, or 6, wherein the male pre-gametes are transplanted into at least one new host recipient before breeding.

16. The method of claim 5 or 6, wherein the founder pair of step (a) is one single inbred breeding pair.

17. The method of claim 7, wherein the pedigreed inbred breeding pair of step (b) is one single inbred breeding pair.

18. The method of claim 5, or 6, wherein the female pre-gametes are ovaries and the ovaries are subdivided into at least 2 fragments per ovary.

19. The method of claim 5, or 6, wherein at least one ovary fragment is transplanted into one new host recipient before breeding.

20. The method of claim 5, or 6, wherein a pedigree-tracked stock of rodent female pre-gametes comprises:

(a) isolating ovaries from the at least one pedigree-tracked founder female of founder female offspring;

(b) sub-dividing the ovaries into fragments, thereby producing ovary fragments; and (c) cryopreserving the ovary fragments of step (b) in containers such that each container comprises ovary fragments from the same female.

21. The method of claim 5, or 6, wherein:

(a) the female pre-gametes are ovaries or ovary fragments that are transplanted into at least one female host recipient, followed by breeding the host female recipient(s) with pedigree-tracked male pre-gametes or gamete(s) isolated from a male founder who is either brother or father to the female from whom the pre-gametes were obtained;

(b) ovaries or ovary fragments from the host female recipient(s) of step (a) are isolated and pedigree-tracked and transplanted into a different host female recipient, who is then bred with pedigree-tracked male gamete(s) isolated from the male founder; and (c) step (b) is repeated at appropriate intervals, thereby extending the gamete potential of the ovary or ovary fragment.

22. The method of claim 21, wherein the female pre-gametes are cryopreserved before breeding.

23. The method of claim 21, wherein the male pre-gametes or gametes are cryopreserved before breeding.

24. The method of claim 21, wherein breeding is by an assisted reproductive technique.

25. The method of claim 24, wherein the assisted reproductive technique is in vitro fertilization, intracytoplasmic sperm injection or artificial insemination.

26. A method of maintaining the genetic stability of a congenic rodent strain, comprising in the order of:

(a) backcrossing, at least once, a congenic founder female or congenic founder male using a breeding partner selected from an appropriate background pedigree-tracked inbred foundation colony, thereby producing backcrossed congenic rodents;

(b) intercrossing the backcrossed congenic rodents by selecting a brother-sister or parent-offspring pair obtained in step (a) to produce rodents homozygous for a congenic marker, to establish a congenic foundation colony;

(c) producing pedigree-tracked rodent embryos by breeding the brother-sister or parent-offspring pair of the congenic foundation colony selected in step (b) and cryopreserving the pedigree-tracked rodent embryos;

(d) producing live rodents from the cryopreserved rodent embryos obtained in step (c);

(e) re-establishing the foundation colony by selecting a pedigreed congenic breeding pair from the live rodents obtained in step (d) and breeding them to produce offspring, wherein the congenic breeding pair is a brother-sister or a parent-offspring pair from which all subsequent rodents of the strain are derived; and (f) replenishing the foundation colony by repeating steps (d) to (e) at intervals of 1 to 20 generations and thus, inhibiting the accumulation of genotypic changes, thereby maintaining genetic stability of the congenic rodent strain.

27. The method of claim 7, wherein:
(a) the ovary or ovary fragments are transplanted into at least one female host recipient, followed by breeding the host female recipient(s) with pedigree-tracked male pre-gametes or gamete(s) isolated from a male founder who is either brother or father to the female from whom the ovary or ovary fragments were obtained;
(b) ovaries or ovary fragments from the host female recipient(s) of step (a) are isolated and pedigree-tracked and transplanted into a different host female recipient, who is then bred with pedigree-tracked male gamete(s) isolated from the male founder; and
(c) step (b) is repeated at appropriate intervals, thereby extending the gamete potential of the ovary or ovary fragment.

28. The method of claim 27, wherein the ovaries or ovary fragments are cryopreserved before breeding.

29. The method of claim 27, wherein the male pre-gametes or gametes are cryopreserved before breeding.

* * * * *

UNITED STATES PATENT AND TRADEMARK OFFICE
CERTIFICATE OF CORRECTION

| | |
|---|---|
| PATENT NO. | : 8,552,254 B2 |
| APPLICATION NO. | : 12/606047 |
| DATED | : October 8, 2013 |
| INVENTOR(S) | : Michael V. Wiles et al. |

It is certified that error appears in the above-identified patent and that said Letters Patent is hereby corrected as shown below:

In the Claims:

Claim 5, Column 44, lines 9-49 should read:

5. A method of maintaining genetic stability of an inbred rodent strain, comprising in the order of:

(a) breeding at least one founder pair to produce at least one female offspring and at least one male offspring, wherein the founder pair is a brother-sister pair or a parent-offspring pair;

(b) obtaining rodent pre-gametes and/or gametes from the at least one female offspring and the at least one male offspring of step (a), thereby producing rodent female pre-gametes and/or gametes and rodent male pre-gametes and/or gametes;

(c) cryopreserving rodent female pre-gametes and/or gametes and rodent male pre-gametes and/or gametes obtained in step (b), thereby producing a pedigree-tracked stock of cryopreserved rodent female pre-gametes and/or gametes and cryopreserved rodent male pre-gametes and/or gametes;

(d) maintaining the stock of cryopreserved rodent female pre-gametes and/or gametes and cryopreserved rodent male pre-gametes and/or gametes produced in step (c);

(e) breeding pedigree-tracked cryopreserved female pre-gametes and/or gametes obtained in step (c) with pedigree-tracked cryopreserved male pre-gametes and/or gametes of step (c) to produce live rodents;

(f) selecting at least one pedigreed inbred breeding pair from the live rodents obtained in step (e) as a new founder pair to re-establish a foundation colony, wherein the new founder pair is a Signed and Sealed this
Twenty-eighth Day of January, 2014

Michelle K. Lee
*Deputy Director of the United States Patent and Trademark Office* brother-sister pair, or a parent-offspring pair from which all subsequent rodents of the strain are derived;

(g) breeding the at least one new founder pair from step (f) to produce offspring and thereby re-establish the foundation colony, wherein the foundation colony is a colony of only brother-sister pairs, parent-offspring pairs or brother-sister pairs and parent-offspring pairs from which all subsequent rodents of the strain are derived; and (h) replenishing the foundation colony by repeating steps (e) to (g) at intervals of 1 to 20 generations and thus, inhibiting the accumulation of genetic changes, thereby maintaining genetic stability of the inbred rodent strain.

Claim 6, column 44, lines 50 - column 45, lines 1-14 should read:

6. A method of maintaining genetic stability of an inbred rodent strain, comprising in the order of:

(a) breeding at least one founder pair to produce at least one female offspring and at least one male offspring, wherein the founder pair is a brother-sister pair or a parent-offspring pair;

(b) isolating a pedigree-tracked stock of rodent pre-gametes and/or gametes, wherein the rodent pre-gametes and/or gametes are obtained from the at least one female offspring and the at least one male offspring of step (a);

(c) breeding the pedigree-tracked stock of rodent pre-gametes and/or gametes of step (b) to produce rodent embryos, and cryopreserving the rodent embryos;

(d) producing live rodents from cryopreserved rodent embryos obtained in step (c);

(e) selecting at least one pedigreed inbred breeding pair from the live rodents obtained in step (d) as a new founder pair to re-establish a foundation colony, wherein the at least one new founder pair is a brother-sister pair, or a parent-offspring pair from which all subsequent rodents of the strain are derived;

(f) breeding the at least one new founder pair from step (e) to produce offspring and thereby re-establish the foundation colony, wherein the foundation colony is a colony of only brother-sister pairs, only parent-offspring pairs or brother-sister pairs and parent-offspring pairs from which all subsequent rodents of the strain are derived; and (g) replenishing a foundation colony by repeating steps (d) to (f) at intervals of 1 to 20 generations and thus, inhibiting the accumulation of genetic changes, thereby maintaining genetic stability of the inbred rodent strain.

Claim 7, column 4, lines 15-45 should read:

7. A method of maintaining genetic stability of an inbred rodent strain, comprising in the order of:

(a) establishing a foundation colony of an inbred rodent strain, wherein the foundation colony comprises only brother-sister pairs, parent-offspring pairs or brother-sister pairs and parent-offspring pairs from which all subsequent rodents of the strain are derived;

(b) selecting at least one pedigreed inbred breeding pair as a founder pair from the foundation colony of step (a), wherein the founder pair is a brother-sister pair or a parent-offspring pair from which all subsequent rodents of the strain are derived;

(c) isolating at least one ovary from the founder female selected in step (b);

(d) transplanting the at least one ovary or at least one fragment of the ovary into a new host recipient;

(e) obtaining rodent embryos by breeding the host recipient obtained in step (d) with the founder male selected in step (b) and cryopreserving the rodent embryos;

(f) producing live rodents from cryopreserved rodent embryos obtained in step (e);

(g) re-establishing the foundation colony by selecting a pedigreed inbred breeding pair from the live rodents obtained in step (f) and breeding them to produce offspring, wherein the inbred breeding pair is a brother-sister pair or a parent-offspring pair from which all subsequent rodents of the inbred strain are derived; and (h) replenishing the foundation colony by repeating steps (f) to (g) at intervals of 1 to 20 generations and thus, inhibiting the accumulation of genetic changes, thereby maintaining genetic stability of the inbred rodent strain.